United States Patent
Gu et al.

(10) Patent No.: US 11,826,358 B2
(45) Date of Patent: Nov. 28, 2023

(54) LOCALLY-INDUCED ADIPOSE TISSUE BROWNING BY MICRONEEDLE PATCH FOR OBESITY TREATMENT

(71) Applicants: NORTH CAROLINA STATE UNIVERSITY, Raleigh, NC (US); THE TRUSTEES OF COLUMBIA UNIVERSITY IN THE CITY OF NEW YORK, New York, NY (US)

(72) Inventors: Zhen Gu, Los Angeles, CA (US); Yuqi Zhang, Raleigh, NC (US); Li Qiang, Closter, NJ (US)

(73) Assignees: NORTH CAROLINA STATE UNIVERSITY, Raleigh, NC (US); THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 570 days.

(21) Appl. No.: 16/646,615

(22) PCT Filed: Sep. 13, 2018

(86) PCT No.: PCT/US2018/050800
§ 371 (c)(1),
(2) Date: Mar. 12, 2020

(87) PCT Pub. No.: WO2019/055594
PCT Pub. Date: Mar. 21, 2019

(65) Prior Publication Data
US 2020/0246321 A1    Aug. 6, 2020

Related U.S. Application Data

(60) Provisional application No. 62/558,348, filed on Sep. 13, 2017.

(51) Int. Cl.
| A61K 31/4439 | (2006.01) |
| A61M 37/00   | (2006.01) |
| A61K 9/00    | (2006.01) |
| A61K 9/51    | (2006.01) |

(52) U.S. Cl.
CPC ..... *A61K 31/4439* (2013.01); *A61M 37/0015* (2013.01); *A61K 9/0021* (2013.01); *A61K 9/5161* (2013.01); *A61M 2037/0023* (2013.01); *A61M 2037/0046* (2013.01)

(58) Field of Classification Search
None
See application file for complete search history.

(56) References Cited

U.S. PATENT DOCUMENTS

| 6,743,211 B1 | 6/2004  | Prausnitz et al. |
| 7,473,247 B2 | 1/2009  | Mikszta et al.   |
| 8,285,390 B2 | 10/2012 | Levinson et al.  |
| 8,523,927 B2 | 9/2013  | Levinson et al.  |
| 8,702,774 B2 | 4/2014  | Baker et al.     |
| 8,708,966 B2 | 4/2014  | Allen et al.     |
| 8,834,547 B2 | 9/2014  | Anderson et al.  |
| 8,840,608 B2 | 9/2014  | Anderson et al.  |
| 9,033,950 B2 | 5/2015  | Smith et al.     |
| 9,050,251 B2 | 6/2015  | Boyden et al.    |
| 9,132,031 B2 | 9/2015  | Levinson et al.  |
| 9,320,782 B2 | 4/2016  | Greene et al.    |
| 9,322,009 B2 | 4/2016  | Greene et al.    |
| 9,325,794 B2 | 4/2016  | Kunniyur et al.  |
| 9,340,780 B2 | 5/2016  | Greene et al.    |
| 9,347,053 B2 | 5/2016  | Greene et al.    |
| 9,358,149 B2 | 6/2016  | Anderson et al.  |
| 9,375,345 B2 | 6/2016  | Levinson et al.  |
| 9,394,547 B2 | 7/2016  | Chen et al.      |
| 9,404,104 B2 | 8/2016  | Greene et al.    |
| 9,422,538 B2 | 8/2016  | Greene et al.    |
| 9,428,743 B2 | 8/2016  | Greene et al.    |
| 9,526,884 B2 | 12/2016 | Yan et al.       |
| 9,540,629 B2 | 1/2017  | Greene et al.    |
| 9,556,425 B2 | 1/2017  | Greene et al.    |
| 9,572,800 B2 | 2/2017  | Zarnitsyn        |
| 9,574,187 B2 | 2/2017  | Greene et al.    |
| 9,580,706 B2 | 2/2017  | Greene et al.    |
| 9,582,103 B2 | 2/2017  | Ando             |
| 9,593,322 B2 | 3/2017  | Greene et al.    |
| 9,593,323 B2 | 3/2017  | Greene et al.    |
| 9,623,093 B2 | 4/2017  | Greene et al.    |
| 9,623,112 B2 | 4/2017  | Gao et al.       |
| 2005/0261632 A1 | 11/2005 | Xu            |
| 2007/0203061 A1 | 8/2007  | Kadowaki et al. |
| 2008/0014583 A1 | 1/2008  | Montminy et al. |

(Continued)

FOREIGN PATENT DOCUMENTS

| IN | 2007DE00086 A | * 7/2008 |
| WO | 2011006087 A1 | 1/2011   |

(Continued)

OTHER PUBLICATIONS

Kim, So Hun, and Jorge Plutzky. "Brown fat and browning for the treatment of obesity and related metabolic disorders." Diabetes & metabolism journal 40.1 (2016): 12-21.
Zaric, Marija, et al. "Dissolving microneedle delivery of nanoparticle-encapsulated antigen elicits efficient cross-priming and Th1 immune responses by murine Langerhans cells." Journal of Investigative Dermatology 135.2 (2015): 425-434.
Zaric, Marija, et al. "Skin dendritic cell targeting via microneedle arrays laden with antigen-encapsulated poly-D, L-lactide-co-glycolide nanoparticles induces efficient antitumor and antiviral immune responses." ACS nano 7.3 (2013): 2042-2055.
Donnelly, Ryan F., et al. "Microneedle-mediated intradermal nanoparticle delivery: potential for enhanced local administration of hydrophobic pre-formed photosensitisers." Photodiagnosis and Photodynamic Therapy 7.4 (2010): 222-231.

(Continued)

*Primary Examiner* — Brian J Davis
(74) *Attorney, Agent, or Firm* — Meunier Carlin & Curfman LLC

(57) ABSTRACT

Disclosed herein are compositions and methods for delivering adipose tissue browning agents and/or fat modulating agents.

19 Claims, 23 Drawing Sheets
Specification includes a Sequence Listing.

(56) References Cited

U.S. PATENT DOCUMENTS

| | | |
|---|---|---|
| 2010/0047332 A1 | 2/2010 | Higashinaka |
| 2013/0122077 A1 | 5/2013 | Al-Ghananeem |
| 2013/0165861 A1 | 6/2013 | Ross |
| 2015/0037422 A1 | 2/2015 | Kaplan et al. |
| 2015/0250891 A1 | 9/2015 | Venkatraman et al. |
| 2016/0377598 A1 | 12/2016 | Kishore et al. |
| 2017/0128707 A1 | 5/2017 | Ross |

FOREIGN PATENT DOCUMENTS

| | | | |
|---|---|---|---|
| WO | 2013/137826 A1 | 9/2013 | |
| WO | 2014068296 A1 | 5/2014 | |
| WO | 2014/179344 A1 | 11/2014 | |
| WO | 2017151727 A1 | 9/2017 | |
| WO | WO 2018/226160 A1 * | 12/2018 | ............... A61K 9/00 |

OTHER PUBLICATIONS

Coulman, Sion A., et al. "Minimally invasive cutaneous delivery of macromolecules and plasmid DNA via microneedles." Current drug delivery 3.1 (2006): 65-75.

International Search Report and Written Opinion issued in corresponding application No. PCT/US2018/050800, dated Nov. 19, 2018, 13 pages.

Larraneta, E. et al. Microneedle arrays as transdermal and intradermal drug delivery systems: Materials science, manufacture and commercial development. Materials Science 8nd Engineering R. 2016. vol. 104.

Au-Yong, I. T.; Thorn, N.; Ganatra, R.; Perkins, A. C.; Symonds, M. E. Brown Adipose Tissue and Seasonal Variation in Humans. Diabetes 2009, 58, 2583-2587.

Bakopanos, E.; Silva, J. E. Thiazolidinediones Inhibit the Expression of Beta3-Adrenergic Receptors at a Transcriptional Level. Diabetes 2000, 49, 2108-2115.

Bartelt, A.; Heeren, J. Adipose Tissue Browning and Metabolic Health. Nat. Rev. Endocrinol. 2014, 10, 24-36.

Bonet, M. L.; Oliver, P.; Palou, A. Pharmacological and Nutritional Agents Promoting Browning of White Adipose Tissue. Biochim. Biophys. Acta, Mol. Cell. Biol. Lipids 2013, 1831, 969-985.

Cai, X.; Jia, X.; Gao, W.; Zhang, K.; Ma, M.; Wang, S.; Zheng, Y.; Shi, J.; Chen, H. A Versatile Nanothera Stic Agent for Efficient Dual-Mode Imaging Guided Synergistic Chemo-Thermal Tumor Therapy. Adv. Funct. Mater. 2015, 25, 2520-2529.

Chang, S.-H.; Stoll, C. R.; Song, J.; Varela, J. E.; Eagon, C. J.; Colditz, G. A. The Effectiveness and Risks of Bariatric Surgery: An Updated Systematic Review and Meta-Analysis, 2003-2012. JAMA Surg. 2014, 149, 275-287.

Cipolletta, D.; Feuerer, M.; Li, A.; Kamei, N.; Lee, J.; Shoelson, S. E.; Benoist, C. Mathis, D. PPARγ is a Major Driver of the Accumulation and Phenotype of Adipose Tissue Treg Cells. Nature 2012, 486, 549-553.

Clapham, J. C.; Arch, J. R.; Tadayyon, M. Anti-Obesity Drugs: a Critical Review of Current Therapies and Future Opportunities. Pharmacol. Ther. 2001, 89, 81-121.

Colman, E.; Golden, J.; Roberts, M.; Egan, A.; Weaver, J.; Rosebraugh, C. The FDA's Assessment of Two Drugs for Chronic Weight Management. New Engl. J. Med. 2012, 367, 1577-1579.

Dietrich, M. O.; Horvath, T. L. Limitations in Anti-Obesity Drug Development: the Critical Role of Hunger-Promoting Neurons. Nat. Rev. Drug Discov. 2012, 11, 675-691.

Friedman, J. M. Obesity: Causes and Control of Excess Body Fat. Nature 2009, 459, 340-342.

Gu, Z.; Aimetti, A. A.; Wang, Q.; Dang, T. T.; Zhang, Y.; Veiseh, O.; Cheng, H.; Langer, R. S.; Anderson, D. G. Injectable Nano-Network for Glucose-Mediated Insulin Delivery. ACS Nano 2013, 7, 4194-4201.

Harms, M.; Seale, P. Brown and Beige Fat: Development, Function and Therapeutic Potential. Nat. Med. 2013, 19, 1252-1263.

Heymsfield, S. B.; Wadden, T. A. Mechanisms, Pathophysiology, and Management of Obesity. New Engl. J. Med. 2017, 376, 1490.

Jiang, T.; Mo, R.; Bellotti, A.; Zhou, J.; Gu, Z. Gel-Liposome-Mediated Co-Delivery of Anticancer Membrane-Associated Proteins and Small-Molecule Drugs for Enhanced Therapeutic Efficacy. Adv. Funct. Mater. 2014, 24, 2295-2304.

Kajimura, S.; Spiegelman, B. M.; Seale, P. Brown and Beige Fat: Physiological Roles Beyond Heat Generation. Cell Metab. 2015, 22, 546-559.

Kalliokoski, O.; Jacobsen, K. R.; Darusman, H. S.; Henriksen, T.; Weimann, A. Poulsen, H. E.; Hau, J.; Abelson, K. S. Mice Do Not Habituate to Metabolism Cage Housing—a Three Week Study of Male BALB/c Mice. PLoS One 2013, 8, e58460.

Klein, J.; Fasshauer, M.; Ito, M.; Lowell, B. B.; Benito, M.; Kahn, C. R. β3-Adrenergic Stimulation Differentially Inhibits Insulin Signaling and Decreases Insulin-Induced Glucose Uptake in Brown Adipocytes. J. Biol. Chem. 1999, 274, 34795-34802.

Kogan, G.; Šoltés, L.; Stern, R.; Gemeiner, P. Hyaluronic Acid: a Natural Biopolymer with a Broad Range of Biomedical and Industrial Applications. Biotechnol. Lett. 2007, 29, 17-25.

Li, D.; Zhang, F.; Zhang, X.; Xue, C.; Namwanje, M.; Fan, L.; Reilly, M. P.; Hu, F.; Qiang, L. Distinct Functions of PPARγ Isoforms in Regulating Adipocyte Plasticity. Biochem. Biophys. Res. Commun. 2016, 481, 132-138.

Lowell, M., PhD, BB; Flier, M., JS. Brown Adipose Tissue, β3-Adrenergic Receptors, and Obesity. Annu. Rev. Med. 1997, 48, 307-316.

Lu, Y.; Aimetti, A. A.; Langer, R.; Gu, Z. Bioresponsive Materials. Nat. Rev. Mater. 2016, 1, 16075.

Mo, R.; Jiang, T.; Di, J.; Tai, W.; Gu, Z. Emerging Micro-and Nanotechnology Based Synthetic Approaches for Insulin Delivery. Chem. Soc. Rev. 2014, 43, 3595-3629.

Nagy, T. R.; Krzywanski, D.; Li, J.; Meleth, S.; Desmond, R. Effect of Group vs. Single Housing on Phenotypic Variance in C57BL/6J Mice. Obesity Res. 2002, 10, 412-415.

Nedergaard, J.; Cannon, B. The Browning of White Adipose Tissue: Some Burning Issues. Cell Metab. 2014, 20, 396-407.

Ogden, C. L.; Carroll, M. D.; Fryar, C. D.; Flegal, K. M. Prevalence of Obesity Among Adults and Youth: United States, 2011-2014. NCHS data brief 2015, 219, 1-8.

W. H.O. Obesity and Overweight. Fact sheet No. 311. 2015. Obesity and overweight. Fact sheet No. 311. Geneva: World Health Organization; Jan. 2015 (http://www.who.int/mediacentre/factsheets/fs311/en/index.html).

Prausnitz, M. R.; Langer, R. Transdermal Drug Delivery. Nat. Biotechnol. 2008, 26, 1261-1268.

Rucker, D.; Padwal, R.; Li, S. K.; Curioni, C.; Lau, D. C. Long Term Pharmacotherapy for Obesity and Overweight: Updated Meta-Analysis. BMJ 2007, 335, 1194-9.

Sun, W.; Hu, Q.; Ji, W.; Wright, G.; Gu, Z. Leveraging Physiology for Precision Drug Delivery. Physiol. Rev. 2017, 97, 189-225.

Vernochet, C.; Peres, S. B.; Davis, K. E.; McDonald, M. E.; Qiang, L.; Wang, H.; Scherer, P. E.; Farmer, S. R. C/EBPα and the Corepressors CtBP1 and CtBP2 Regulate Repression of Select Visceral White Adipose Genes During Induction of the Brown Phenotype in White Adipocytes by Peroxisome Proliferator-Activated Receptor γ Agonists. Mol. Cell. Biol. 2009, 29, 4714-4728.

Voikar, V.; Polus, A.; Vasar, E.; Rauvala, H. Long-Term Individual Housing in C57BL/6J and DBA/2 Mice: Assessment of Behavioral Consequences. Genes Brain Behav. 2005, 4, 240-252.

Wang, C.; Ye, Y.; Hochu, G. M.; Sadeghifar, H.; Gu, Z. Enhanced Cancer Immunotherapy by Microneedle Patch-Assisted Delivery of Anti-PD1 Antibody. Nano Lett. 2016, 16, 2334-2340.

Weyer, C.; de Souza, C. J. Development of β3-Adrenoceptor Agonists as Antiobesity and Antidiabetes Drugs in Humans: Current Status and Future Prospects. Drug Dev. Res. 2000, 51, 80-93.

Weyer, C.; Gautier, J.; Danforth Jr, E. Development of Beta 3-Adrenoceptor Agonists for the Treatment of Obesity and Diabetes An Update. Diabetes Metab. 1999, 25, 11-21.

Whittle, A.; Relat-Pardo, J.; Vidal-Puig, A. Pharmacological Strategies for Targeting BAT Thermogenesis. Trends Pharmacol. Sci. 2013, 34, 347-355.

(56) References Cited

OTHER PUBLICATIONS

Wu, J.; Cohen, P.; Spiegelman, B. M. Adaptive Thermogenesis in Adipocytes: Is Beige the New Brown? Genes Dev. 2013, 27, 234-250.

Xue, Y.; Xu, X.; Zhang, X.-Q.; Farokhzad, O. C.; Langer, R. Preventing Diet-Induced Obesity in Mice by Adipose Tissue Transformation and Angiogenesis Using Targeted Nanoparticles. Proc. Natl. Acad. Sci. U.S.A. 2016, 5552-5557.

Ye, Y.; Yu, J.; Wang, C.; Nguyen, N. Y.; Walker, G. M.; Buse, J. B.; Gu, Z. Microneedles Integrated with Pancreatic Cells and Synthetic Glucose-Signal Amplifiers for Smart Insulin Delivery. Adv. Mater. 2016, 28, 3115-3121.

Yu, J.; Zhang, Y.; Bomba, H.; Gu, Z. Stimuli-Responsive Delivery of Therapeutics for Diabetes Treatment. Bioeng. Transl. Med. 2016, 1, 323-337.

Yu, J.; Zhang, Y.; Ye, Y.; DiSanto, R.; Sun, W.; Ranson, D.; Ligler, F. S.; Buse, J. B.; Gu, Z. Microneedle-Array Patches Loaded with Hypoxia-Sensitive Vesicles Provide Fast Glucose-Responsive Insulin Delivery. Proc. Natl. Acad. Sci. U.S.A. 2015, 112, 8260-8265.

Yu, S.; Gavrilova, O.; Chen, H.; Lee, R.; Liu, J.; Pacak, K.; Parlow, A.; Quon, M. J.; Reitman, M. L.; Weinstein, L. S. Paternal versus Maternal Transmission of a Stimulatory G-Protein α Subunit Knockout Produces Opposite Effects on Energy Metabolism. J. Clin. Invest. 2000, 105, 615-623.

Zhang, Y.; Yu, J.; Shen, Q.; Gu, Z. Glucose-Responsive Synthetic Closed-Loop Insulin Delivery Systems. Prog. Chem. 2015, 27, 11-26. English Abstract included in text.

Zhang, Y.; Yu, J.; Wang, J.; Hanne, N. J.; Cui, Z.; Qian, C.; Wang, C.; Xin, H.; Cole, J. H.; Gallippi, C. M. Thrombin-Responsive Transcutaneous Patch for Auto-Anticoagulant Regulation. Adv. Mater. 2017, 29, 1604043.

International Preliminary Report on Patentability issued for Application No. PCT/US2018/050800, dated Mar. 26, 2020.

Dangol, M., et al., "Anti-obesity effect of a novel caffeine-loaded dissolving microneedle patch in high-fat diet-induced obese C57BL/6J mice," Journal of Controlled Release, vol. 265, 2017, pp. 41-47.

Office Action, dated Feb. 9, 2023, received in connection with corresponding CN Patent Application No. 201880073636.5 (and English translation).

* cited by examiner

SEQUENCE LISTING

<160> NUMBER OF SEQ ID NOS: 36

<210> SEQ ID NO 1
<211> LENGTH: 19
<212> TYPE: DNA
<213> ORGANISM: Artificial Sequence
<220> FEATURE:
<223> OTHER INFORMATION: Synthetic construct

<400> SEQUENCE: 1
catgctcggc cctacatgg                                                   19

<210> SEQ ID NO 2
<211> LENGTH: 21
<212> TYPE: DNA
<213> ORGANISM: Artificial Sequence
<220> FEATURE:
<223> OTHER INFORMATION: Synthetic construct

<400> SEQUENCE: 2
cacagagtcg tcatccgtca c                                                21

<210> SEQ ID NO 3
<211> LENGTH: 22
<212> TYPE: DNA
<213> ORGANISM: Artificial Sequence
<220> FEATURE:
<223> OTHER INFORMATION: Synthetic construct

<400> SEQUENCE: 3
gcactggcaa gttctactgc aa                                               22

<210> SEQ ID NO 4
<211> LENGTH: 23
<212> TYPE: DNA
<213> ORGANISM: Artificial Sequence
<220> FEATURE:
<223> OTHER INFORMATION: Synthetic construct

<400> SEQUENCE: 4
gtaggtgaag agaacggcct tgt                                              23

<210> SEQ ID NO 5
<211> LENGTH: 23
<212> TYPE: DNA
<213> ORGANISM: Artificial Sequence
<220> FEATURE:
<223> OTHER INFORMATION: Synthetic construct

<400> SEQUENCE: 5
acaccgagat ttccttcaaa ctg                                              23

<210> SEQ ID NO 6
<211> LENGTH: 25
<212> TYPE: DNA
<213> ORGANISM: Artificial Sequence
<220> FEATURE:
<223> OTHER INFORMATION: Synthetic construct

<400> SEQUENCE: 6
ccatctaggg ttatgatgct cttca                                            25

<210> SEQ ID NO 7
<211> LENGTH: 21
<212> TYPE: DNA
<213> ORGANISM: Artificial Sequence

```
<220> FEATURE:
<223> OTHER INFORMATION: Synthetic construct

<400> SEQUENCE: 7
tgctcttctg tatcgcccag t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
gccgtgttaa ggaatctgct g                                              21

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
cagcgtcatg gtcagtctgt                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
agaaaaccgt gtggcagaga                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
gaaccatgaa gccaacgact                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
gcgaagttca cagtggttcc                                                20

<210> SEQ ID NO 13
<211> LENGTH: 24
<212> TYPE: DNA
<213> ORGANISM: Artificial Sequence
<220> FEATURE:
<223> OTHER INFORMATION: Synthetic construct

<400> SEQUENCE: 13
tatctgcact gccaagactg agtg                                           24
```

```
<210> SEQ ID NO 14
<211> LENGTH: 23
<212> TYPE: DNA
<213> ORGANISM: Artificial Sequence
<220> FEATURE:
<223> OTHER INFORMATION: Synthetic construct

<400> SEQUENCE: 14
cttcttgctg gtcttgccat tcc                                              23

<210> SEQ ID NO 15
<211> LENGTH: 18
<212> TYPE: DNA
<213> ORGANISM: Artificial Sequence
<220> FEATURE:
<223> OTHER INFORMATION: Synthetic construct

<400> SEQUENCE: 15
agagtggagg cgcatgct                                                    18

<210> SEQ ID NO 16
<211> LENGTH: 22
<212> TYPE: DNA
<213> ORGANISM: Artificial Sequence
<220> FEATURE:
<223> OTHER INFORMATION: Synthetic construct

<400> SEQUENCE: 16
ggcatctagg aggaagctgt tc                                               22

<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
ccaacaacga tgagcaacag                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18 cggggttaaaa atggacctga                                                 20

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
ttccatccag ttgccttctt                                                  20

<210> SEQ ID NO 20
<211> LENGTH: 20
<212> TYPE: DNA
<213> ORGANISM: Artificial Sequence
<220> FEATURE:
<223> OTHER INFORMATION: Synthetic construct
```

<400> SEQUENCE: 20
atttccacga tttcccagag                                               20

<210> SEQ ID NO 21
<211> LENGTH: 18
<212> TYPE: DNA
<213> ORGANISM: Artificial Sequence
<220> FEATURE:
<223> OTHER INFORMATION: Synthetic construct

<400> SEQUENCE: 21
ggcctggacg acaaaacc                                                 18

<210> SEQ ID NO 22
<211> LENGTH: 18
<212> TYPE: DNA
<213> ORGANISM: Artificial Sequence
<220> FEATURE:
<223> OTHER INFORMATION: Synthetic construct

<400> SEQUENCE: 22
caggatgggc tccatgac                                                 18

<210> SEQ ID NO 23
<211> LENGTH: 19
<212> TYPE: DNA
<213> ORGANISM: Artificial Sequence
<220> FEATURE:
<223> OTHER INFORMATION: Synthetic construct

<400> SEQUENCE: 23
ccctgccatt gttaagacc                                                19

<210> SEQ ID NO 24
<211> LENGTH: 19
<212> TYPE: DNA
<213> ORGANISM: Artificial Sequence
<220> FEATURE:
<223> OTHER INFORMATION: Synthetic construct

<400> SEQUENCE: 24
tgctgctgtt cctgttttc                                                19

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
agaagcggtg aaccactgat                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic construct

<400> SEQUENCE: 26
gaatgcgagt ggtcttccat                                               20

<210> SEQ ID NO 27

<211> LENGTH: 21
<212> TYPE: DNA
<213> ORGANISM: Artificial Sequence
<220> FEATURE:
<223> OTHER INFORMATION: Synthetic construct

<400> SEQUENCE: 27
tctgggagat tctcctgttg a                                             21

<210> SEQ ID NO 28
<211> LENGTH: 20
<212> TYPE: DNA
<213> ORGANISM: Artificial Sequence
<220> FEATURE:
<223> OTHER INFORMATION: Synthetic construct

<400> SEQUENCE: 28
ggtgggccag aatggcatct                                               20

<210> SEQ ID NO 29
<211> LENGTH: 22
<212> TYPE: DNA
<213> ORGANISM: Artificial Sequence
<220> FEATURE:
<223> OTHER INFORMATION: Synthetic construct

<400> SEQUENCE: 29
tggccttcat cacctctctg aa                                            22

<210> SEQ ID NO 30
<211> LENGTH: 23
<212> TYPE: DNA
<213> ORGANISM: Artificial Sequence
<220> FEATURE:
<223> OTHER INFORMATION: Synthetic construct

<400> SEQUENCE: 30
tttctgatcc acggctcctg tga                                           23

<210> SEQ ID NO 31
<211> LENGTH: 23
<212> TYPE: DNA
<213> ORGANISM: Artificial Sequence
<220> FEATURE:
<223> OTHER INFORMATION: Synthetic construct

<400> SEQUENCE: 31
aagaaccttt catttcccct cct                                           23

<210> SEQ ID NO 32
<211> LENGTH: 23
<212> TYPE: DNA
<213> ORGANISM: Artificial Sequence
<220> FEATURE:
<223> OTHER INFORMATION: Synthetic construct

<400> SEQUENCE: 32
gtccagcaat ttaagccaat gtt                                           23

<210> SEQ ID NO 33
<211> LENGTH: 20
<212> TYPE: DNA
<213> ORGANISM: Artificial Sequence
<220> FEATURE:
<223> OTHER INFORMATION: Synthetic construct

<400> SEQUENCE: 33

```
tgtcgaatta ccactgctgg                                            20

<210> SEQ ID NO 34
<211> LENGTH: 20
<212> TYPE: DNA
<213> ORGANISM: Artificial Sequence
<220> FEATURE:
<223> OTHER INFORMATION: Synthetic construct

<400> SEQUENCE: 34
ctgtgaaggg aatcaaggga                                            20

<210> SEQ ID NO 35
<211> LENGTH: 21
<212> TYPE: DNA
<213> ORGANISM: Artificial Sequence
<220> FEATURE:
<223> OTHER INFORMATION: Synthetic construct

<400> SEQUENCE: 35
actgccacac ctccagtcat t                                          21

<210> SEQ ID NO 36
<211> LENGTH: 21
<212> TYPE: DNA
<213> ORGANISM: Artificial Sequence
<220> FEATURE:
<223> OTHER INFORMATION: Synthetic construct

<400> SEQUENCE: 36
ctttgcctca ctcaggattg g                                          21
```

LOCALLY-INDUCED ADIPOSE TISSUE BROWNING BY MICRONEEDLE PATCH FOR OBESITY TREATMENT

This is a national stage application of PCT International Application No. PCT/US2018/050800, filed on Sep. 13, 2018, entitled "Locally-Induced Adipose Tissue Browning by Microneedle Patch for Obesity Treatment," which claims the benefit of, U.S. Provisional Application No. 62/558,348, filed on Sep. 13, 2017, each of which is fully incorporated herein by reference in its entirety.

STATEMENT REGARDING FEDERALLY SPONSORED RESEARCH

This invention was made with government support under Grant Numbers DK063608, DK097455, and TR001111 awarded by the National Institutes of Health. The Government has certain rights in the invention.

BACKGROUND

Obesity has been classified as a disease by the American Medical Association in 2013 and recognized as one of the most serious public health problems in the $21^{st}$ century along with the rapid global socioeconomic development. Obesity-associated disorders such as type-2 diabetes, cardiovascular diseases, and cancer, have become a global threat to human health. Particularly in the United States, more than one-third of the adult population are obese, and the prevalence is going to roar in the next decades. Current treatments for obesity include restriction of calorie intake by diet programs, promoting energy expenditure through physical exercise, pharmacological therapy, as well as bariatric surgeries and liposuction. However, most therapeutics come with undesired side effects on human organs such as gastrointestine, liver, and kidney, and surgeries involve high risks. Therefore, there is an urgent requirement to exploit effective treatments for obesity. The compositions and methods disclosed herein address these and other needs.

SUMMARY

Disclosed herein are particles comprising: an adipose tissue browning agent and/or fat modulating agent. In one aspect, the adipose tissue browning agent can comprise rosiglitazone (Rosi), CL 316243, or any combination thereof.

In one aspect, the particles of any preceding aspect can further comprising a pH-altering agent (such as for example, an agent that reduces pH), a peroxide-metabolizing enzyme (such as, for example catalase), and/or a pH-responsive matrix. In one aspect, the pH-altering agent can comprise a glucose responsive enzyme (such as, for example, glucose oxidase (GOx).

Also disclosed herein are particles of any preceding aspect, wherein the pH-responsive matrix is degradable in a relatively acidic pH compared to physiological pH. In one aspect, the pH responsive matrix can comprise a polymer such as a polymer of dextran monomers (for example a polymer of m-dextran monomers).

In one aspect, disclosed herein are particles of any preceding aspect, further comprising a encapsulating material (such as, for example, a surfactant or other polymer) that encapsulates the pH responsive matrix. In one aspect, the encapsulating material can comprise alginate, a polysaccharide (for example chitosan) and/or polymers comprising polyvinylpyrrolidine.

In one aspect, disclosed herein are devices for the transport of a material across a biological barrier of a subject comprising the nanoparticle of any preceding aspect. In one aspect, disclosed herein are devices for transport of a material across a biological barrier of a subject comprising a plurality of microneedles each having a base end and a tip; a substrate to which the base ends of the microneedles are attached or integrated; and a plurality of particles comprising an adipose tissue browning agent and/or fat modulating agent.

Also disclosed herein are devices of any preceding aspect, wherein the plurality of particles are attached to the plurality of microneedles.

In one aspect, disclosed herein are devices of any preceding aspect, wherein the plurality of microneedles comprises a biocompatible polymer (such as, for example, methacrylated hyaluronic acid (m-HA)). In one aspect, biocompatible polymer can be crosslinked. Also disclosed herein are devices of any preceding aspect, wherein the plurality of microneedles have a center-to-center interval of about 200 μm to about 800 μm and/or wherein the plurality of microneedles have a height of about 600 nm to 1.8 μm.

In one aspect disclosed herein are methods of locally delivering an adipose tissue browning agent and/or fat modulating agent (also referred to herein as a fat modulator) comprising providing a device for transport of a material across a biological barrier of a subject comprising: a plurality of microneedles each having a base end and a tip; a substrate to which the base ends of the microneedles are attached or integrated; and a plurality of particles comprising an adipose tissue browning and/or fat modulating agent; and administering the device to a subject in need of an adipose tissue browning and/or fat modulating agent. In one aspect, the delivery of the browning agent to white adipose tissue can convert at least a portion of the subdermal white adipose tissue to brown adipose tissue. In one aspect delivery of the fat modulating agent can induce apoptosis, lipid uptake, lipolysis, or kill fat cells.

In one aspect, disclosed herein are methods of locally delivering an adipose tissue browning agent and/or fat modulating agent of any preceding aspect, wherein the device is administered to a location of the subject's body, the location comprising subdermal white adipose tissue. Also disclosed are methods of locally delivering an adipose tissue browning agent and/or fat modulating agent of any preceding aspect and/or fat modulating agent, wherein the administering step b) comprises inserting the plurality of microneedles into a biological barrier.

In one aspect, disclosed herein are methods of locally delivering an adipose tissue browning agent and/or fat modulating agent of any preceding aspect, wherein the plurality of particles further comprises a pH altering agent and a pH-responsive matrix. In one aspect, the pH altering agent can decrease the pH within the nanoparticles, and wherein the decrease in pH degrades the pH-responsive matrix and releases the adipose tissue browning agent and/or fat modulating agent. In one aspect, disclosed herein are methods of locally delivering an adipose tissue browning agent and/or fat modulating agent of any preceding aspect wherein the device releases the adipose tissue browning agent and/or fat modulating agent in hyperglycemic conditions.

Also disclosed herein are methods of treating a disease (such as, for example obesity or diabetes) in a subject in need thereof comprising providing a device for transport of a material across a biological barrier of a subject comprising: a plurality of microneedles each having a base end and a tip; a substrate to which the base ends of the microneedles are attached or integrated; and a plurality of particles comprising an adipose tissue browning agent and/or fat modulating agent; and administering the device to a subject in need of treating a disease. In one aspect, the methods of treating a disease (such as, for example obesity or diabetes) can reduce the subject's subdermal white adipose tissue.

In one aspect disclosed herein are methods of treating a disease of any preceding aspect, wherein the administering step b) comprises inserting the plurality of microneedles into a biological barrier. Also disclosed herein are methods of treating of any preceding aspect wherein the plurality of particles further comprises a pH altering agent and a pH-responsive matrix. In one aspect, the pH altering agent decreases the pH within the nanoparticles, and wherein the decrease in pH degrades the pH-responsive matrix and releases the adipose tissue browning agent and/or fat modulating agent.

Also disclosed herein are methods of treating a disease of any preceding aspect, wherein the administering step b) modulates (for example, increases) expression of one or more brown adipocyte genes (such as, for example Ucp1, Dio1, Elovl3, Cidea, Pgc-1α, Cox7a1, or Cox8b), adiponectin, and/or PPARγ target aP2.

In one aspect, disclosed herein are methods of treating of any preceding aspect, wherein the method decreases expression of one or more white adipocyte genes. Also disclosed herein are methods of treating of any preceding aspect, wherein the method increases energy expenditure and fatty acid oxidation of the subject, increases insulin sensitivity and/or avoids significant skin lesions.

BRIEF DESCRIPTION OF THE DRAWINGS

The accompanying figures, which are incorporated in and constitute a part of this specification, illustrate several aspects described below.

FIG. 2A shows the average hydrodynamic sizes of Rosi NPs determined by DLS. FIG. 2B shows the relevant pH changes of dextran NPs with or without GOx in PBS buffer in the presence of 100 mg/dL glucose. (n=3) FIG. 2C shows in vitro accumulated Rosi release from the acid-degradable dextran NPs (w/or w/o GOx) in PBS buffer containing 100 mg/dL glucose at 37° C. (n=3) FIG. 2D shows UV absorbance of NPs suspensions $A_{400}$ nm. (n=3) FIG. 2E shows SEM images of Rosi NPs incubated in PBS buffer with 100 mg/dL glucose at 37° C. on day 0 and day 4 (scale bar: 2 μm), inserted pictures show the transparency change of the NPs suspension. FIG. 2F shows comparable adipogenesis between Rosi NPs- and Rosi compound-treated PgKO-MEFs as assessed by aP2 and Perilipin gene expression. (n=4). FIG. 2G shows the same level of browning induced by Rosi NPs or Rosi compound in the mature 3T3-L1 white adipocytes. (n=4). FIG. 2H shows SEM image of the MN array (scale bar: 200 μm). FIG. 2I shows higher magnification of SEM imaging of MN tip confirmed that the MN was loaded with NPs (scale bar: 10 μm). FIG. 2J shows SEM image of MNs 3 days post administration. FIG. 2K shows trypan blue staining image of mouse skin administered with MN patch (scale bar: 1 mm). Error bars indicate standard deviation (SD), two-tailed Student's t-test, *P<0.05, **P<0.01.

FIG. 3A shows hematoxylin and eosin (H&E)-stained section of the cross-sectional mouse inguinal adipose tissue treated with HA empty MN patch (left), Rosi NP-loaded MN patch (middle), and CL 316243 NP-loaded MN patch (right) (scale bar: 25 μm). FIG. 3B shows Q-PCR analysis of gene expression in inguinal WAT treated with MN patches loaded with HA empty vehicle (EV), Rosi, or CL 316243 (CL). NP-loaded MN patch. Error bars indicate standard error of the mean (SEM), two-tailed Student's t-test, *P<0.05, **P<0.01 compared to EV (n=6).

FIG. 4A shows the body weight change after the 6-day treatment. FIG. 4B shows normalized inguinal fat pad size. FIG. 4C shows normalized epididymal fat pad size. FIG. 4D shows the average food intake during the treatment. FIG. 4E shows the locomotor activity during one 24-h dark/light cycle. The panel on the right is the area under curve (AUC). FIG. 4F shows oxygen consumption and AUC. FIG. 4G shows respiration exchange ratio (RER) and AUC during one dark/light cycle. Error bars indicate SEM, two-tailed Student's t-test, *P<0.05, **P<0.01 compared to EV (n=6).

FIG. 5A shows a picture illustrating mice treated with browning agent patch on one inguinal side (red) and empty vehicle patch on the other side (blue). FIG. 5B shows normalized body weight of mice without treatment or treated with browning agent patches. FIG. 5C shows an IPGTT test in mice 2 weeks post-treatment. FIG. 5D shows blood glucose levels of mice treated with browning agent patches or empty patches after 16 h fasting. FIG. 5E shows normalized epididymal fat pad size in mice with different treatments. FIG. 5F shows normalized weight of interscapular fat pad size in mice with different treatments. FIG. 5G shows the ratio of the treated inguinal fat pad size to untreated side. FIG. 5H shows photos of two sides of inguinal adipose tissues from obese mice 4-weeks post treatment. FIG. 5I shows H&E staining of inguinal adipose tissues (scale bar: 50 μm). FIG. 5J shows Q-PCR analysis of adipocyte gene expressions in inguinal tissues. b-g, Error bars indicate SD, two-tailed Student's t-test, *P<0.05, **P<0.01 compared to EV (n=5); j, Error bars indicate SEM, two-tailed Student's t-test, *P<0.05, **P<0.01 compared to EV (n=5).

DETAILED DESCRIPTION

Figure 1:
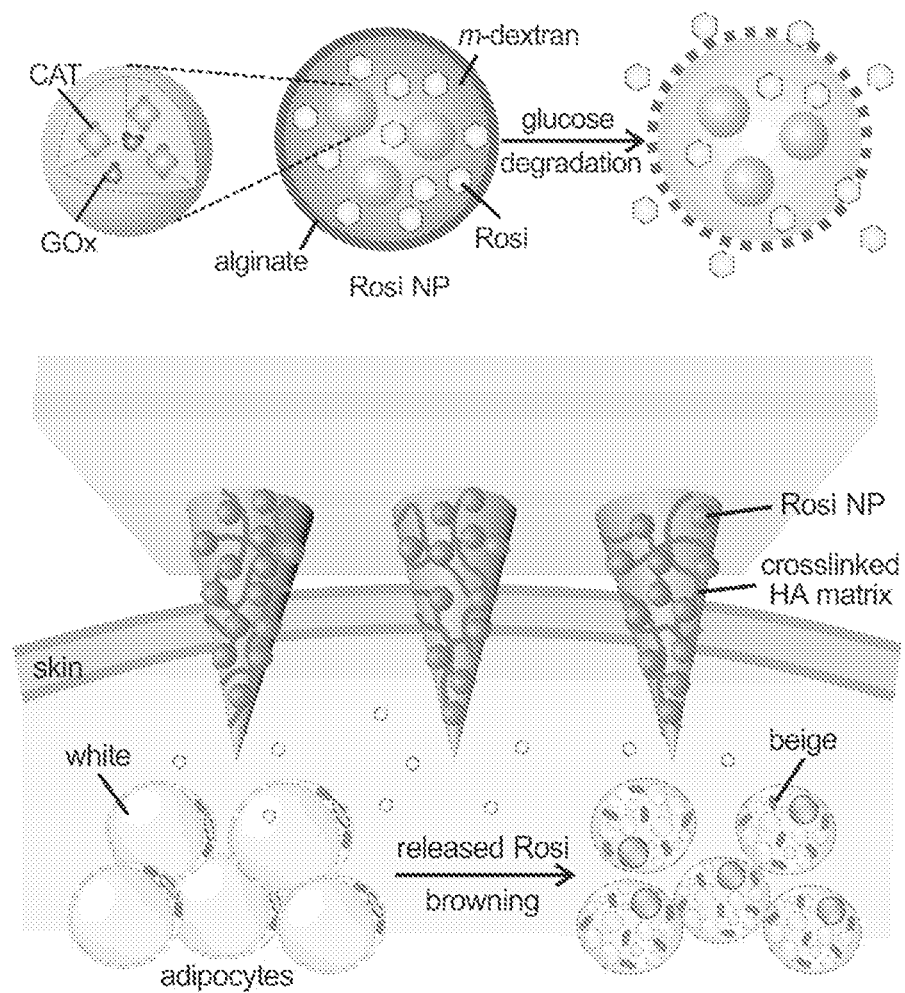
FIG. 1 shows a schematic depicting a browning agents-loaded transcutaneous MN patch. Nanoparticles (NPs) encapsulating rosiglitazone (Rosi), glucose oxidase (GOx), and catalase (CAT) are prepared from pH-sensitive acetal-modified dextran and coated with alginate. NPs are further loaded into the microneedle-array patch made of crosslinked hyaluronic acid (HA) matrix for brown-remodeling of white fat.

Disclosed herein are novel controlled-release nanoparticle compositions that provide physiologically relevant levels of therapeutic, prophylactic, locally to the site of administration.

Reference will now be made in detail to the embodiments of the invention, examples of which are illustrated in the drawings and the examples. The present disclosure may, however, be embodied in many different forms and should not be construed as limited to the embodiments set forth herein.

Terminology

Unless defined otherwise, all technical and scientific terms used herein have the same meaning as commonly understood to one of ordinary skill in the art to which this invention belongs. The following definitions are provided for the full understanding of terms used in this specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In one non-limiting embodiment, the terms are defined to be within 10% of the associated value provided. In another non-limiting embodiment, the terms are defined to be within 5%. In still another non-limiting embodiment, the terms are defined to be within 1%.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, "modulate" means to effectuate a change (either an increase or a decrease) in the amount of gene expression, protein expression, amount of a symptom, disease, composition, condition, or activity.

An "increase" can refer to any change that results in a greater gene expression, protein expression, amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller gene expression, protein expression, amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

A "control" is an alternative subject or sample used in an experiment for comparison purposes. A control can be "positive" or "negative."

"Controlled release" or "sustained release" refers to release of an agent from a given dosage form in a controlled fashion in order to achieve the desired pharmacokinetic profile in vivo. An aspect of "controlled release" agent delivery is the ability to manipulate the formulation and/or dosage form in order to establish the desired kinetics of agent release.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

"Peptide," "protein," and "polypeptide" are used interchangeably to refer to a natural or synthetic molecule comprising two or more amino acids linked by the carboxyl group of one amino acid to the alpha amino group of another.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Primer" or "DNA primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in "PCR: A PRACTICAL APPROACH" (M. MacPherson et al., IRL Press at Oxford University Press (1991)). All processes of producing replicate copies of a polynucleotide, such as PCR or gene cloning, are collectively referred to herein as "replication." A primer can also be used as a probe in hybridization reactions, such as Southern or Northern blot analyses. Sambrook et al., supra.

"Polymer" refers to a relatively high molecular weight organic compound, natural or synthetic, whose structure can be represented by a repeated small unit, the monomer. Non-limiting examples of polymers include polyethylene, rubber, cellulose. Synthetic polymers are typically formed by addition or condensation polymerization of monomers. The term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., Type 1 diabetes). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Publications cited herein are hereby specifically incorporated by reference in their entireties and at least for the material for which they are cited.

Recent studies have revealed a crucial role of brown adipose tissue (BAT), a primary heat generation organ, in energy expenditure in mammals. White adipose tissue (WAT) stores exceeded energy as triglycerides, leading to overweight; whereas BAT dissipates energy by producing heat through nonshivering thermogenesis, which may facilitate the suppression of obesity. The transformation of WAT into BAT provides an alternative approach for the treatment of obesity and related metabolic disorders. A variety of genes and pathways that regulate adipocyte development have been identified. However, numerous browning agents (for example, Thiazolidinediones such as, for example, Rosiglitazone and/or Pioglitazone) that can promote "browning" on WAT face challenges in clinical application because of undesired side effects on other organs as a result of a broad targeting spectrum. The compositions disclosed herein accomplish this goal. Thus, in one aspect disclosed herein are methods of reducing the side effects of adipose tissue modulators and/or browning agents including but not limited to Thiazolidinediones (such as, for example, Rosiglitazone and/or Pioglitazone), sibutramine, lorcaserine, and/or orlistat or any other adipose tissue modulator or browning agent disclosed herein comprising providing a device for transport of a material across a biological barrier of a subject comprising: a plurality of microneedles each having a base end and a tip; a substrate to which the base ends of the microneedles are attached or integrated; and a plurality of particles comprising the adipose tissue browning agent and/or fat modulating agent.

In one aspect, disclosed herein are particles comprising: an adipose tissue browning agent. As used herein, a browning agent refers to an agent that induces the conversion of WAT to BAT. Examples of adipose tissue browning agents include, but are not limited to β-adrenergic agonists, leptin, TLQP-21, brain-derived neurothrophic factor, prostaglandins, cardiac natriuretic peptides, PPARγ ligands, PPARα ligands, retinoids, thyroid hormones, AMPK activators, Irisin, fibroblast growth factor 21, and bone morphogenetic protein (M. L. Bonet et al, Biochimica et Biophysica Acta 1831, 969-985 (2013)). Preferred browning agents include PPARγ activators (e.g. Rosiglitazone, (RS)-5-[4-(2-[methyl (pyridin-2-yl)amino]ethoxy)benzyl]thiazolidine-2,4-dione, Pioglitazone, (RS)-5-(4-[2-(5-ethylpyridin-2-yl)etlioxy]benzyi)thiazolidine-2,4-dione, Troglitazone, (RS)-5-(4-[(6-hydroxy-2,5,7,8-tetramethylchroman-2-yl)methoxy]benzyl) thiazolidine-2,4-dione etc.), prostagladin E2 analog (PGE2, (5Z,11a,13E,15S)-7-[3-hydroxy-2-(3-hydroxyoct-1-enyl)-5-oxo-cyclopentyl]hept-5-enoic acid etc.), beta3 adrenoceptor agonist (CL 316243, Disodium 5-[(2R)-2-[[(2R)-2-(3-Chlorophenyl)-2-hydroxyethyl]amino]propyl]-1,3-benzodioxole-2,2-dicarboxylate hydrate, etc.), Fibroblast Growth Factor 21 (FGF-21), and/or Irisin.

In one aspect, disclosed herein are microparticles comprising a fat modulating agent. As used herein, a fat modulating agent (also referred to as a fat modulator or adipose tissue modulator) can comprise any chemical, RNA, DNA, protein that can induce lipid uptake, lipolysis, and/or apoptosis to simply kill the fat cells locally. Examples of lipid modulators include, but are not limited to INVOKANA®, FARXIGA®, JARDIANCE®, STEGLATRO®, orlistat, Sibutramine, Diethylpropion, Phentermine, lorcaserin, Naltrexone, Liraglutide, niacin receptor agonists (including, but not limited to niacin, acipimox, aceifran, (D)β-hydroxybutyrate, 1-alkyl-benzotriazole-5-carboxylic acid, and xanthine derivatives), hormone sensitive lipase inhibitors (such as, for example, -phenyl-5-alkoxy-1,3,4-oxadiazol-2-ones, and 5-(2H)-isoxazolonyl) ureas), β-Adrenergic Receptors (such as, for example, Rafabegron (AJ-9677) and L-796568), A1 receptor agonists, phosphatidylcholine and deoxycholate derivates, Pitavastatin, Benzafibrate, Gemfibrazil, corticosteroids (such as, for example, dexamethasone), cyclic AMP (cAMP) activators (such as, for example, isobutylmethylxanthine), and statins.

In one aspect, the particles can further comprising a pH-altering agent (such as for example, an agent that reduces pH), a peroxide-metabolizing enzyme (such as, for example catalase), and/or a pH-responsive matrix. In one aspect, the pH-altering agent can comprise a glucose responsive enzyme (such as, for example, glucose oxidase (GOx).

It is understood and herein contemplated that the particles may have any desired size for the intended use. For example, the particles may have any diameter from 10 nm to 1,000 nm. The particle can have a diameter from 10 nm to 900 nm, from 10 nm to 800 nm, from 10 nm to 700 nm, from 10 nm to 600 nm, from 10 nm to 500 nm, from 20 nm from 500 nm, from 30 nm to 500 nm, from 40 nm to 500 nm, from 50 nm to 500 nm, from 50 nm to 400 nm, from 100 nm to 400 nm, from 150 nm to 400 nm, or from 175 nm to 400 nm. In preferred embodiments the particles can have a diameter less from about 200 nm to about 300 nm, more preferably from about 225 to about 275. For example, in one aspect the particles can have a diameter less than 275 nm, such as about 250 nm.

Also disclosed herein are particles comprising an adipose tissue browning agent and/or fat modulating agent, wherein the micelle is degradable in a relatively acidic pH compared to physiological pH (approximately between 7.35-7.45). For example, the pH can be reduced to a pH of 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, or 4.0. In one aspect, the pH responsive matrix can comprise a polymer such as a polymer of dextran monomers (for example a polymer of m-dextran monomers).

In one aspect, disclosed herein are particles, further comprising encapsulating material (such as, for example, a surfactant or other polymer) that encapsulates the pH responsive matrix. In one aspect, the encapsulating material can comprise alginate, a polysaccharide (for example chitosan), and/or polymers comprising polyvinylpyrrolidine. In one aspect, disclosed herein are devices for the transport of a material across a biological barrier of a subject comprising the nanoparticle disclosed herein.

Thus, in one aspect, disclosed herein are devices for transport of a material across a biological barrier of a subject comprising a plurality of microneedles each having a base end and a tip; a substrate to which the base ends of the microneedles are attached or integrated; and a plurality of particles comprising an adipose tissue browning agent and/or fat modulating agent.

It is understood and herein contemplated that the adipose tissue browning agents and/or fat modulating agents, pH-altering agent (such as for example, an agent that reduces pH), a peroxide-metabolizing enzyme (such as, for example catalase), surfactants, and/or a pH-responsive matrix of the disclosed particles can each individually or in combination provide be toxic to the tissue of a subject contact with the particle. Accordingly, it is understood and herein contemplated that controlled release over time and limited release to the vicinity of administration (i.e., not systemic) can decrease the toxic effects of the particles. Thus, in one aspect, the plurality of particles are attached to the plurality of microneedles.

It is understood and herein contemplated plurality of microneedles can comprise a biocompatible polymer (such as, for example, methacrylated hyaluronic acid (m-HA)). In one aspect, biocompatible polymer can be crosslinked. Such polymers can also serve to slowly release the adipose browning agent and/or fat modulating agent into tissue. As used herein biocompatible polymers include, but are not limited to polysaccharides; hydrophilic polypeptides; poly (amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly (hydroxyalkylmethacrylamide); poly(hydroxyalkylmethacrylate); poly(saccharides); poly(hydroxy acids); poly(vinyl alcohol), polyhydroxyacids such as poly(lactic acid), poly (glycolic acid), and poly (lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof. Biocompatible polymers can also include polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly (isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate, poly vinyl chloride polystyrene and polyvinylpyrrolidone, derivatives thereof, linear and branched copolymers and block copolymers thereof, and blends thereof. Exemplary biodegradable polymers include polyesters, poly(ortho esters), poly(ethylene amines), poly(caprolactones), poly(hydroxybutyrates), poly(hydroxyvalerates), polyanhydrides, poly(acrylic acids), polyglycolides, poly(urethanes), polycarbonates, polyphosphate esters, polyphospliazenes, derivatives thereof, linear and branched copolymers and block copolymers thereof, and blends thereof.

In some embodiments the particle contains biocompatible and/or biodegradable polyesters or polyanhydrides such as poly(lactic acid), poly(glycolic acid), and poly(lactic-co-glycolic acid). The particles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide$_5$ collectively referred to herein as "PLA", and caprolactone units, such as poly(e-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker. In one aspect, the polymer comprises at least 60, 65, 70, 75, 80, 85, 89, 90, 91, 92, 93, 94, 95, 96, 97, 98, or 99 percent acetal pendant groups.

In one aspect, the disclosed devices can comprise a plurality of microneedles, wherein the plurality of microneedles have a center-to-center interval of about 200 μm to about 800 μm, for example a center to center interval of about 200, 225, 250, 275, 300, 325, 350, 375, 400, 425, 450, 475, 500, 525, 550, 575, 600, 625, 650, 675, 700, 725, 750, 775, or 800 μm.

It is also understood and herein contemplated that the disclosed plurality of microneedles in the disclosed devices is effective when the length of the needle is sufficiently long to reach desired tissues below the dermal layer. Thus, in one aspect, disclosed herein are devices wherein the plurality of microneedles have a height of about 600 nm to 1.8 μm. For example, the plurality of microneedles can have a height of about 600, 650, 700, 750, 800, 850, 900, 950 nm, 1.0, 1.1, 1.2, 1.3, 1.4, 1.5, 1.6, 1.7, or 1.8 μm.

In one aspect disclosed herein are methods of locally delivering a drug (such as, for example, an adipose tissue browning agent and/or fat modulating agent) to adipose tissue comprising providing a device for transport of a material across a biological barrier of a subject comprising: a plurality of microneedles each having a base end and a tip; a substrate to which the base ends of the microneedles are attached or integrated; and a plurality of particles comprising an adipose tissue browning agent and/or fat modulating agent; and administering the device to a subject in need of an adipose tissue browning agent and/or fat modulating agent. In one aspect, the delivery of the browning agent to white adipose tissue can convert at least a portion of the subdermal white adipose tissue to brown adipose tissue. In another aspect, the fat modulating agent can induce lipolysis, lipid uptake, or apoptosis.

In one aspect, disclosed herein are methods of locally delivering a drug (such as, for example, an adipose tissue browning agent and/or fat modulating agent) to adipose tissue, wherein the device is administered to a location of the subject's body, the location comprising subdermal white adipose tissue. Also disclosed are methods of locally delivering an adipose tissue browning agent and/or fat modulating agent, wherein the administering step b) comprises inserting the plurality of microneedles into a biological barrier.

In one aspect, disclosed herein are methods of locally delivering a drug (such as, for example, an adipose tissue browning agent and/or fat modulating agent) to adipose tissue, wherein the plurality of particles further comprises a pH altering agent and a pH-responsive matrix. In one aspect, the pH altering agent can decrease the pH within the nanoparticles, and wherein the decrease in pH degrades the pH-responsive matrix and releases the adipose tissue browning agent and/or fat modulating agent. In one aspect, disclosed herein are methods of locally delivering an adipose tissue browning agent and/or fat modulating agent wherein the device releases the adipose tissue browning agent and/or fat modulating agent in hyperglycemic conditions.

Also disclosed herein are methods of treating a disease (such as, for example obesity or diabetes) in a subject in need thereof comprising providing a device for transport of a material across a biological barrier of a subject comprising: a plurality of microneedles each having a base end and a tip; a substrate to which the base ends of the microneedles are attached or integrated; and a plurality of particles comprising an adipose tissue browning agent and/or fat modulating agent; and administering the device to a subject in need of treating a disease. In one aspect, the methods of treating a disease (such as, for example obesity or diabetes) can reduce the subject's subdermal white adipose tissue.

In some embodiments, "obesity" refers to a body mass index (BMI) of 30 kg/m$^2$ or more (National Institute of Health, Clinical Guidelines on the Identification, Evaluation, and Treatment of Overweight and Obesity in Adults (1998)). However, in some embodiments of the present invention, at least in part, is also intended to include a disease, disorder, or condition that is characterized by a body mass index (BMI) of 25 kg/m$^2$ or more, 26 kg/m$^2$ or more, 27 kg/m$^2$ or more, 28 kg/m$^2$ or more, 29 kg/m$^2$ or more, 29.5 kg m$^2$ or more, or 29.9 kg m or more, all of which are typically referred to as overweight (National Institute of Health, Clinical Guidelines on the Identification, Evaluation, and Treatment of Overweight and Obesity in Adults (1998)). The obesity may be due to any cause, whether genetic or environmental. In one embodiment, "treatment of obesity" refers to preventing obesity or an obesity-associated disorder from occurring if the treatment is administered prior to the onset of the obese condition. Moreover, if treatment is commenced in subjects already suffering from or having symptoms of obesity or an obesity-associated disorder, such treatment is expected to prevent, or to prevent the progression of obesity or the obesity-associated disorder.

The term "obesity-associated disorder" includes all disorders associated with or caused at least in part by obesity. Obesity-associated disorders include, for example, diabetes; cardiovascular disease; high blood pressure; deep vein thrombosis; osteoarthritis; obstructive sleep apnea; cancer and non-alcoholic fatty liver disease.

"Type I diabetes" refers to the form of diabetes mellitus resulting from the autoimmune destruction of insulin-producing cells and reduction of the body's ability to produce insulin. The loss of insulin results in increased blood sugar.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

In one aspect disclosed herein are methods of treating any disease disclosed herein (such as, for example obesity or diabetes), wherein the administering step b) comprises inserting the plurality of microneedles into a biological barrier. Also disclosed herein are methods of treating any disease disclosed herein (such as, for example obesity or diabetes) wherein the plurality of particles further comprises a pH altering agent and a pH-responsive matrix. In one aspect, the pH altering agent decreases the pH within the nanoparticles, and wherein the decrease in pH degrades the pH-responsive matrix and releases the adipose tissue browning agent and/or fat modulating agent.

Also disclosed herein are methods of treating any disease disclosed herein (such as, for example obesity or diabetes), wherein the administering step b) modulates (for example, increases) expression of one or more brown adipocyte genes (such as, for example Ucp1, Dio1, Elovl3, Cidea, Pgc-1α, Cox7a1, or Cox8b), adiponectin, and/or PPARγ target aP2.

In one aspect, disclosed herein are methods of treating any disease disclosed herein (such as, for example obesity or diabetes), wherein the method decreases expression of one or more white adipocyte genes. Also disclosed herein are methods of treating any disease disclosed herein (such as, for example obesity or diabetes), wherein the method increases energy expenditure and fatty acid oxidation of the subject, increases insulin sensitivity and/or avoids significant skin lesions.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1

Herein disclosed is a locally induced browning technology which can include a degradable microneedle (MN)

patch consisted of drug-loaded nanoparticles (NPs) and a crosslinked matrix (FIG. 1). Rosiglitazone (Rosi) or CL 316243 was loaded in the NPs as the model browning agents. The NPs can be further integrated into a microneedle (MN)-array based transdermal device for sustained drug delivery into subcutaneous adipose tissue. The MN patch provides a localized, convenient and painless administration method. In mouse models, the MN patch locally delivers browning agents in a safe and effective manner for inhibition of adipocyte hypertrophy and consequent improvement of metabolism.

Results and Discussion

Synthesis and Characterization of Rosi-Loaded NPs.

Figure 2A:
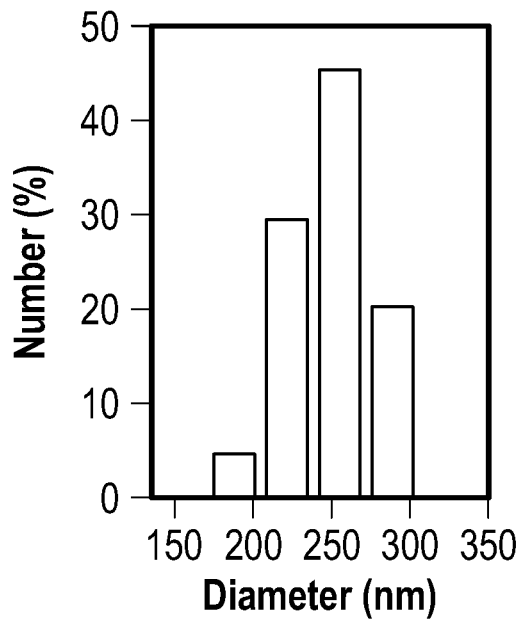
FIGS. 2A-2K show a set of graphs and micrographs depicting fabrication and characterization of browning agent microneedles.
Figure 2B:
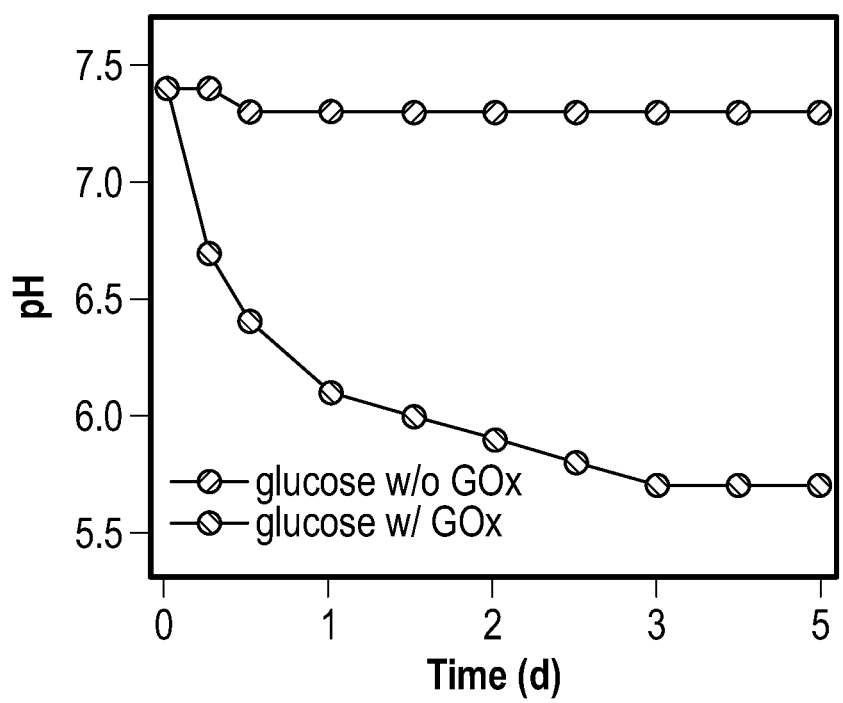
Figure 2C:
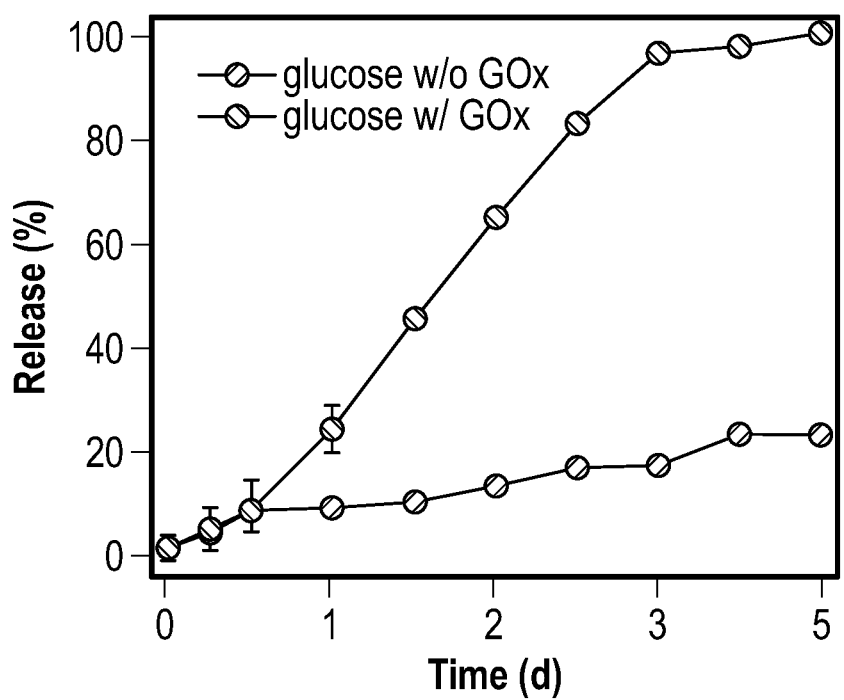
Figure 2D:
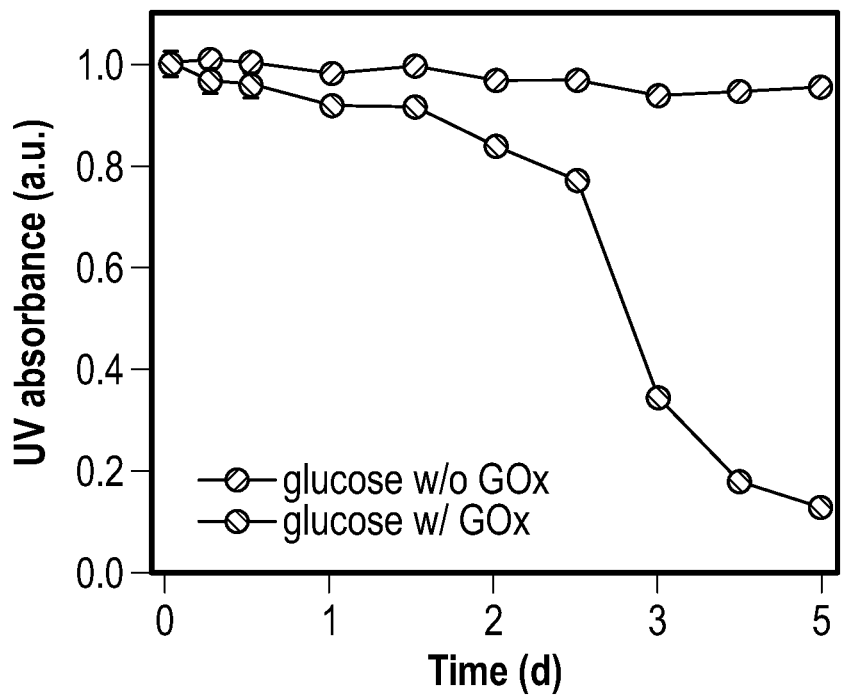
Figure 2E:
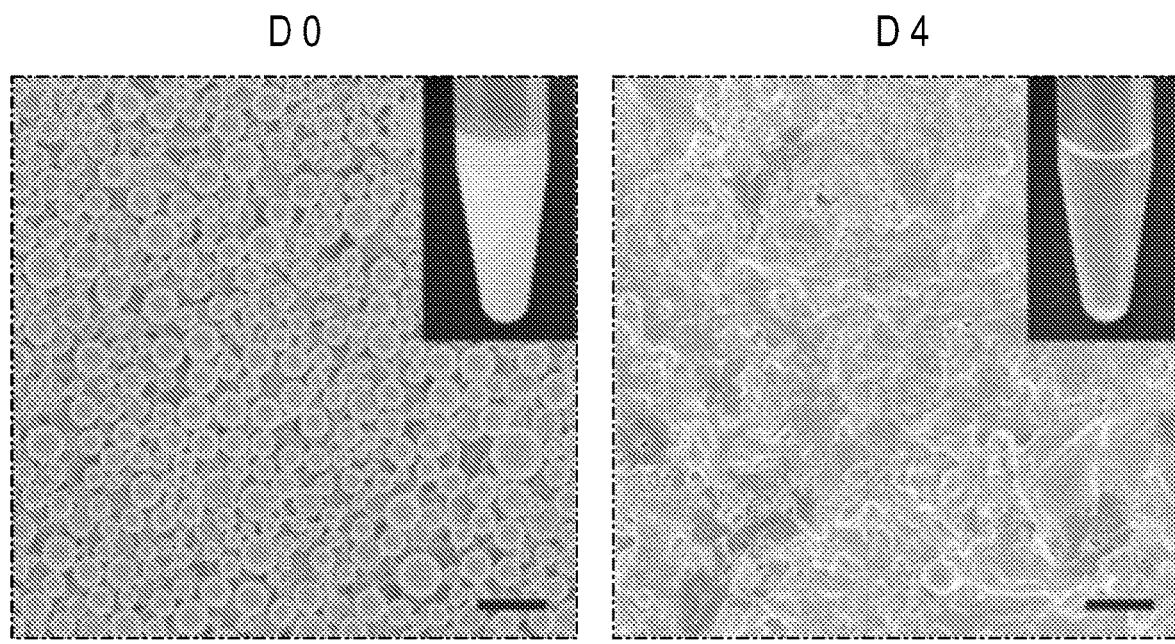
Figure 6:
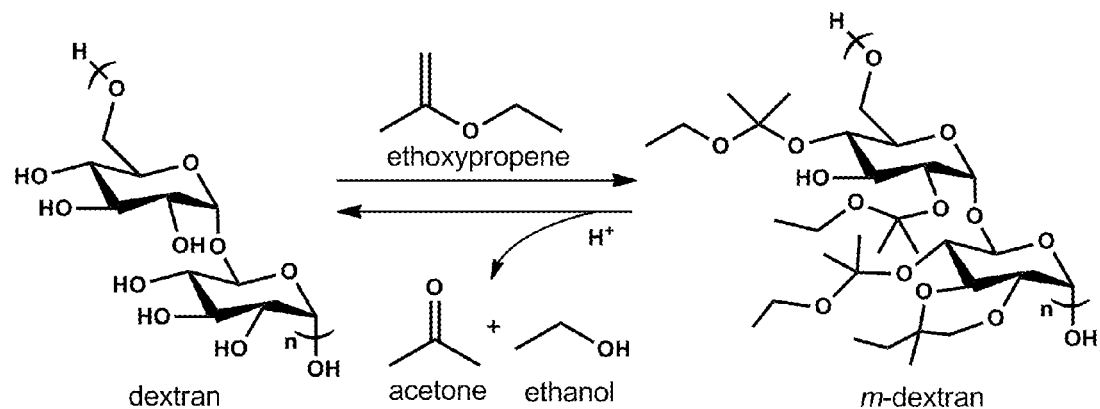
FIG. 6 shows a schematic depicting the synthesis and dissociation routes of m-dextran.

Degradable NPs were prepared using an acid-sensitive dextran derivative by a double emulsion method. The acid-sensitive dextran was synthesized through conjugation with ethoxypropene via an acid-catalyzed reaction, which rendered the derived dextran (m-dextran) with 89% substitution of hydroxyl to pendant acetals (FIG. 6). Rosi, an agonist of Peroxisome Proliferator-Activated Receptor gamma (PPARγ), stimulates adipose tissue transformation by upregulating uncoupling proteins, VEGF, and angiopoietin-like 4. Rosi was encapsulated in dextran NPs for WAT browning. Two enzymes, glucose oxidase (GOx) and catalase (CAT), were introduced into the system to generate acidic environment under the physiological glucose concentration. GOx is able to convert glucose to gluconic acid to decrease the local pH; while CAT helps consume undesired hydrogen peroxide produced during the GOx-mediated enzymatic reaction. The resulting NPs had spherical shapes with monodisperse distribution, as shown by scanning electron microscopy (SEM) (FIG. 2e). The hydrodynamic particle size was around 250 nm, as determined by dynamic light scattering (DLS) (FIG. 2a). The NPs had a loading capacity of 5.2 weight percent and encapsulated efficiency was around 55 percent. To monitor the release kinetics of Rosi, NPs were incubated in PBS buffer containing glucose at a normoglycemic level (100 mg/dL) in the human body. Then, NPs gradually disassociated in the enzyme-induced acidic environment, triggering release of the encapsulated drug (FIG. 2b). NPs with GOx gradually degraded in 3 days, as shown by the reduction of UV absorbance at 400 nm (FIG. 2d), and subsequently released the embedded drug (FIG. 2c, e). To the contrary, insignificant drug was collected from NPs without GOx.

Figure 2F:
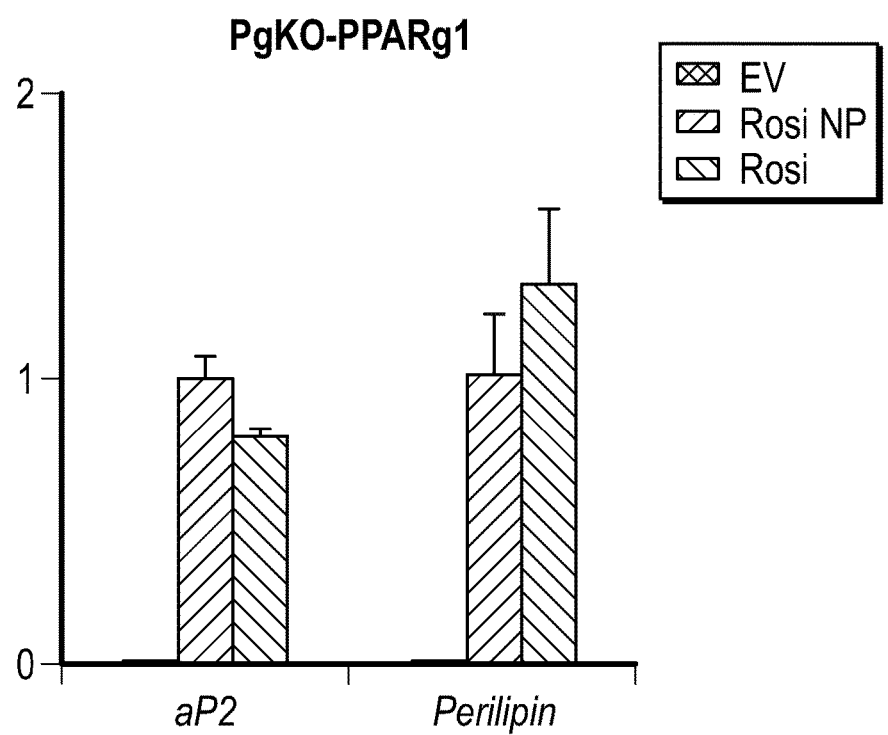
Figure 2G:
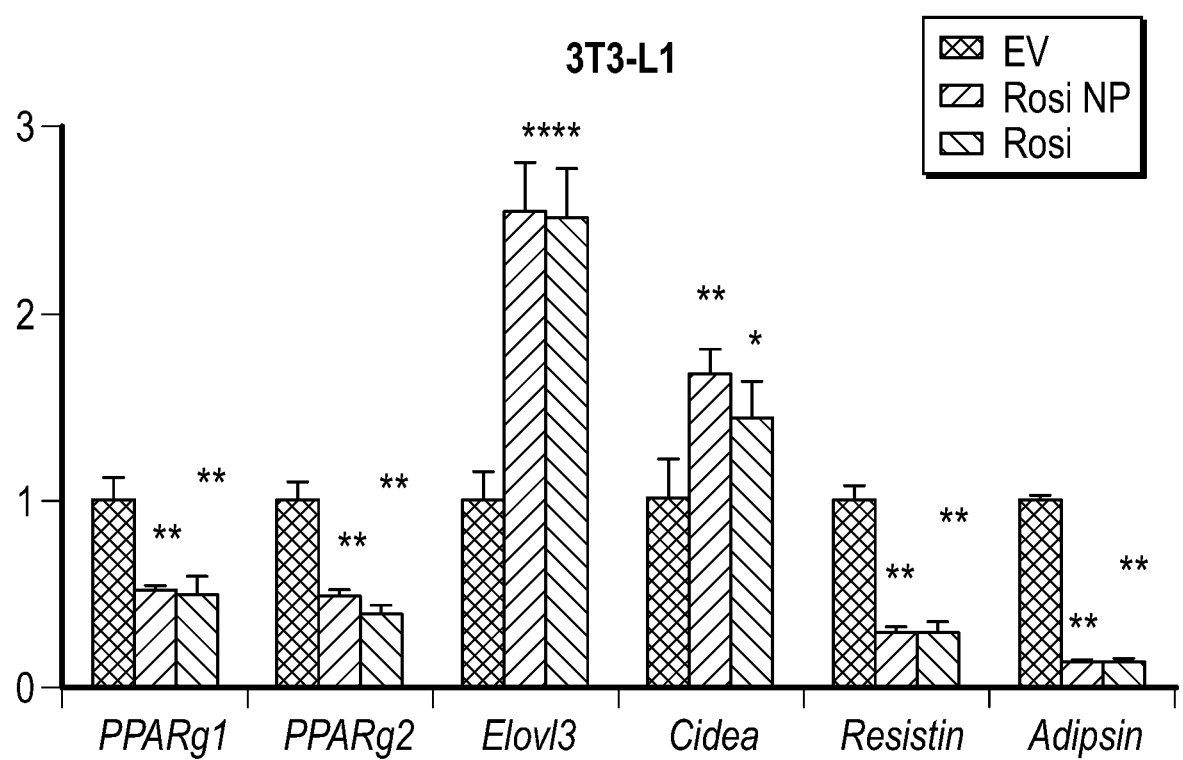

To validate the efficiency of Rosi NPs, an in vitro adipocyte model PgKO-PPARγ1 was used in which the reconstitution of a shorter form of PPARγ (γ1) in Ppar$^{-/-}$ mouse embryonic fibroblast (MEF) rescues adipocyte differentiation only in the presence of exogenous Thiazolidinedione class of ligand (e.g. Rosi). Rosi NPs were as efficient as nude Rosi to induce adipocyte formation, as shown by the same induction of lipid droplet-binding protein genes aP2 and Perilipin (FIG. 2f), both of which are canonical PPARγ target genes. In addition to adipogenic potential, the browning capacity of Rosi NPs was also compared. In fully differentiated 3T3-L1 adipocytes, Rosi NPs behaved the same as nude Rosi to up-regulate brown adipocyte markers Elovl3 and Cidea as well as to repress white adipocyte genes Resistin and Adipsin (FIG. 2g). Therefore, the disclosed nanoparticalization strategy can sustain a constant release of Rosi at physiological levels of glucose without affecting its efficiency.

Fabrication and Characterization of Browning Agent MN-Array Patch.

Figure 2H:
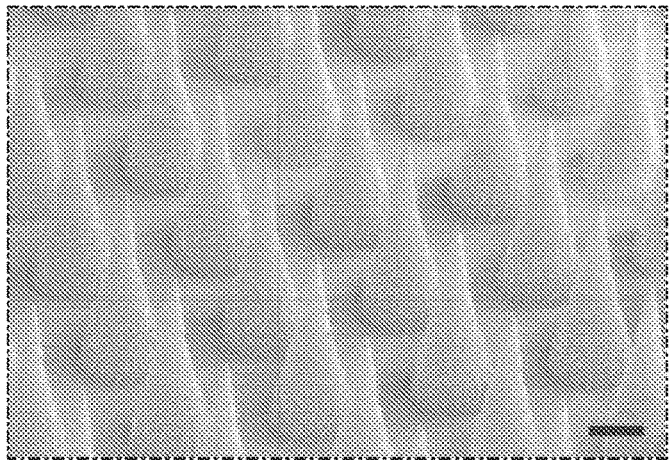
Figure 2I:
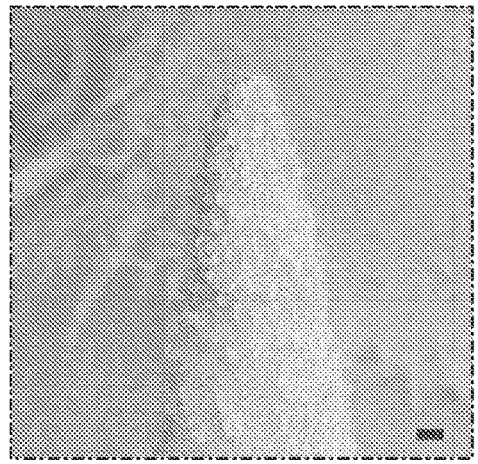
Figure 7:
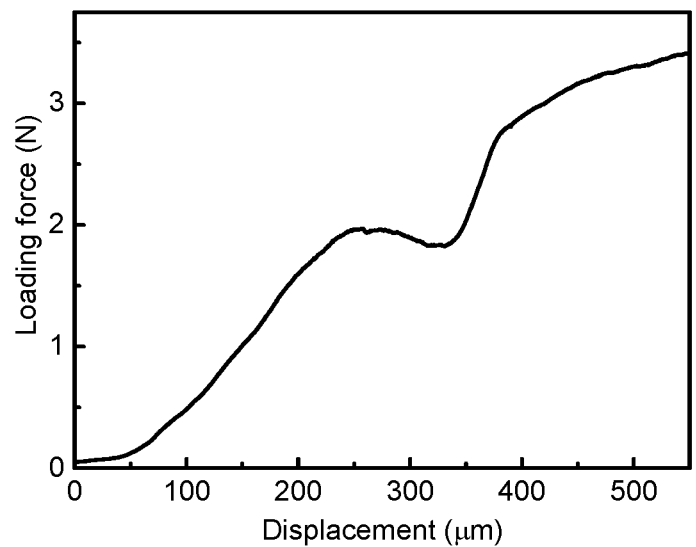
FIG. 7 shows a graph depicting the mechanical behavior of one NP-loaded MN.

NPs were embedded into a polymeric MN-array patch for local delivery of browning agents. Briefly, NPs were first loaded into the tip region of a silicone MN-mold by centrifugation, followed by addition of base solution. Methacrylated HA (m-HA) was selected as the base material, considering its good biocompatibility and mechanical properties. The m-HA base solution was mixed with the crosslinker N,N'-methylenebis(acrylamide) (MBA), and a photoinitiator was further crosslinked through a polymerization reaction upon exposure to UV light (365 nm, 9 mW/cm$^2$ for 30 s). The crosslinked HA-based matrix can enhance the stiffness of the MNs (FIG. 7) for efficient penetration through the skin, as well as facilitate sustained release of drug from the MN tips, which helps maintain local constitutive high drug concentrations in adipose tissues. The MN-array contained 121 needles in a 7×7 mm$^2$ patch with a center-to-center interval of 600 μm. Each MN had a conical shape, in which the MN had a base diameter of about 300 μm and a height of about 800 μm (FIG. 2h). A zoomed SEM image showed the distribution of NPs in the tip (FIG. 2i).

In Vivo Studies of the MNs on Lean Mice.

Figure 2J:
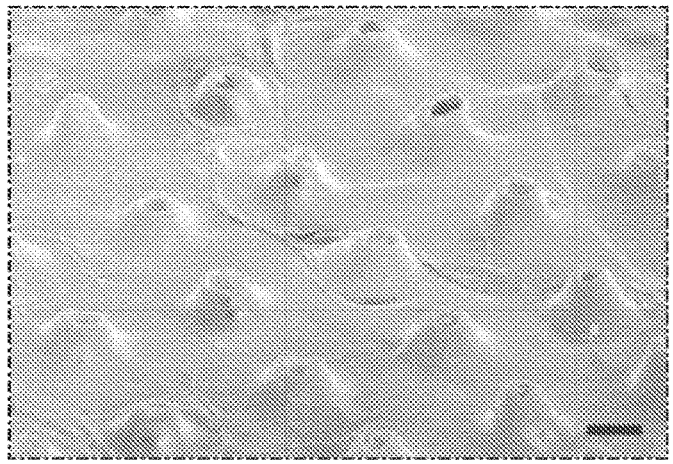
Figure 2K:
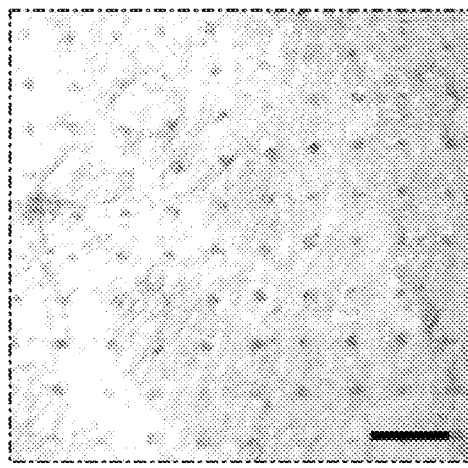
Figures 3A, 3B:
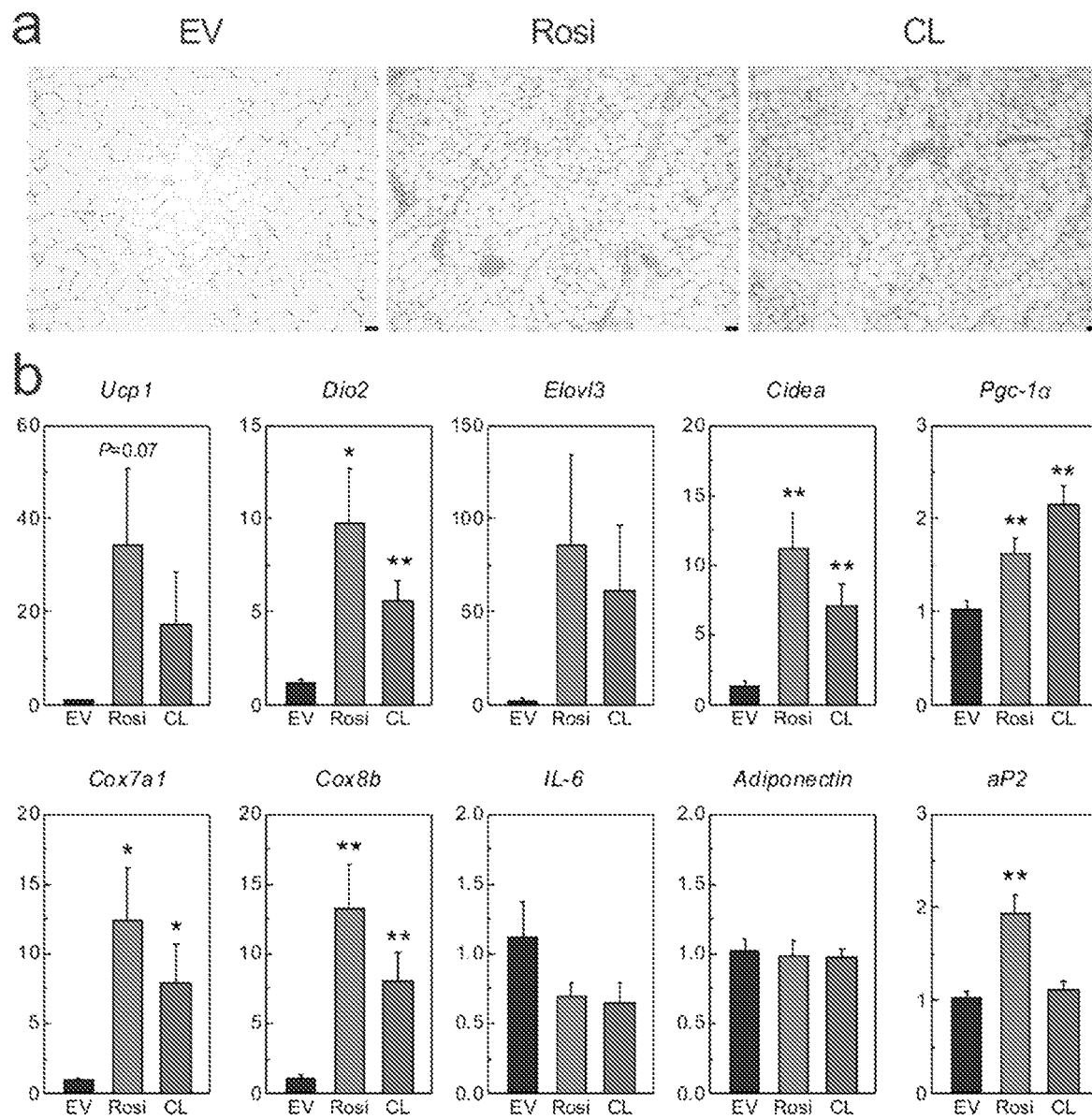
FIGS. 3A and 3B show a set of micrographs and bar charts depicting in vivo browning induction by MN patches in the lean mice.
Figure 8:
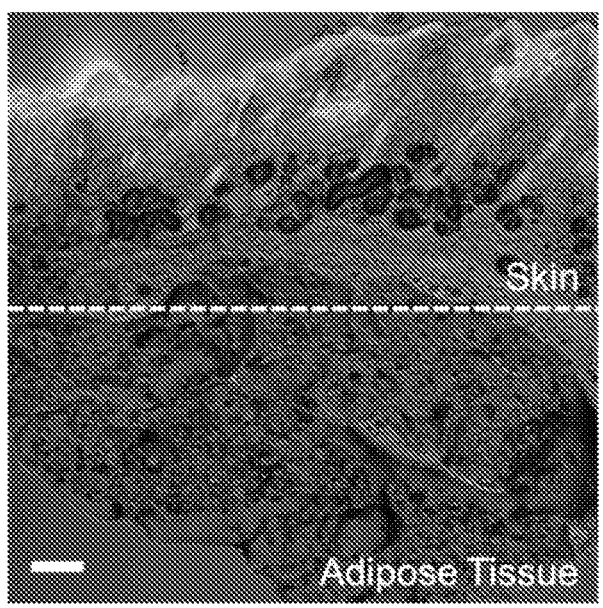
FIG. 8 shows a fluorescence microscopy image of inguinal adipose tissue section after treatment of fluorescein isothiocyanate (FITC)-encapsulated NP through the microneedle patch (scale bar: 200 μm).
Figure 9:
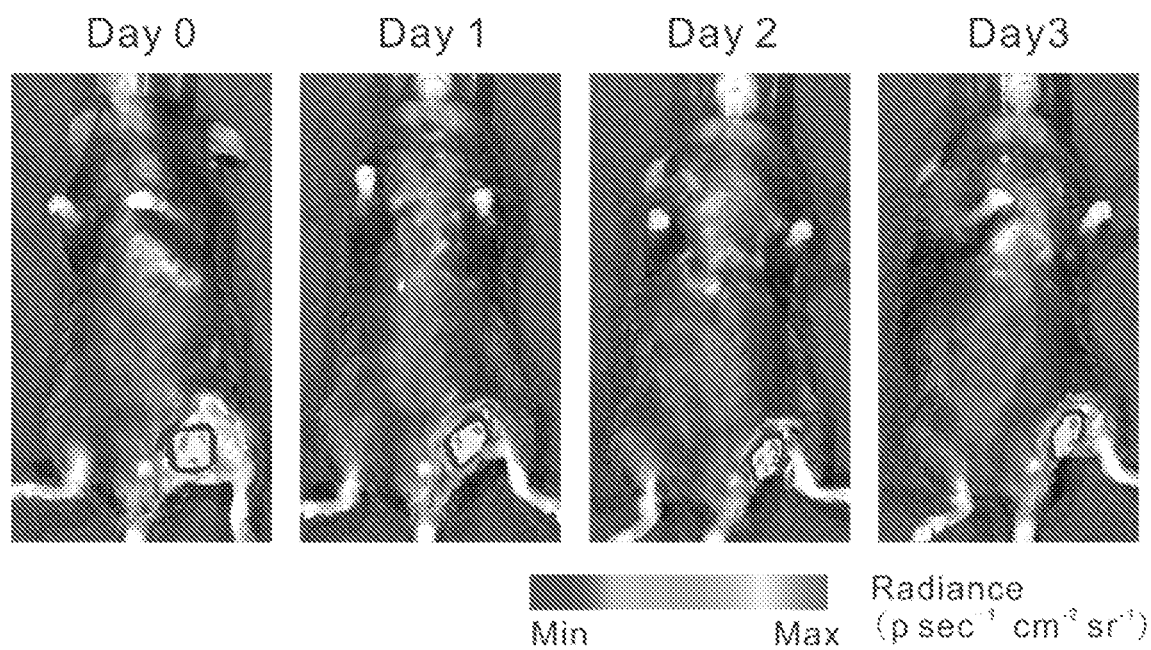
FIG. 9 shows an image of in vivo fluorescence of a mouse treated with Cy5.5-labelled NPs-loaded MNs at different time points. Cy5.5-labelled non-degradable NPs without glucose specific enzyme (GOx) were loaded into crosslinked HA MNs.
Figure 10:
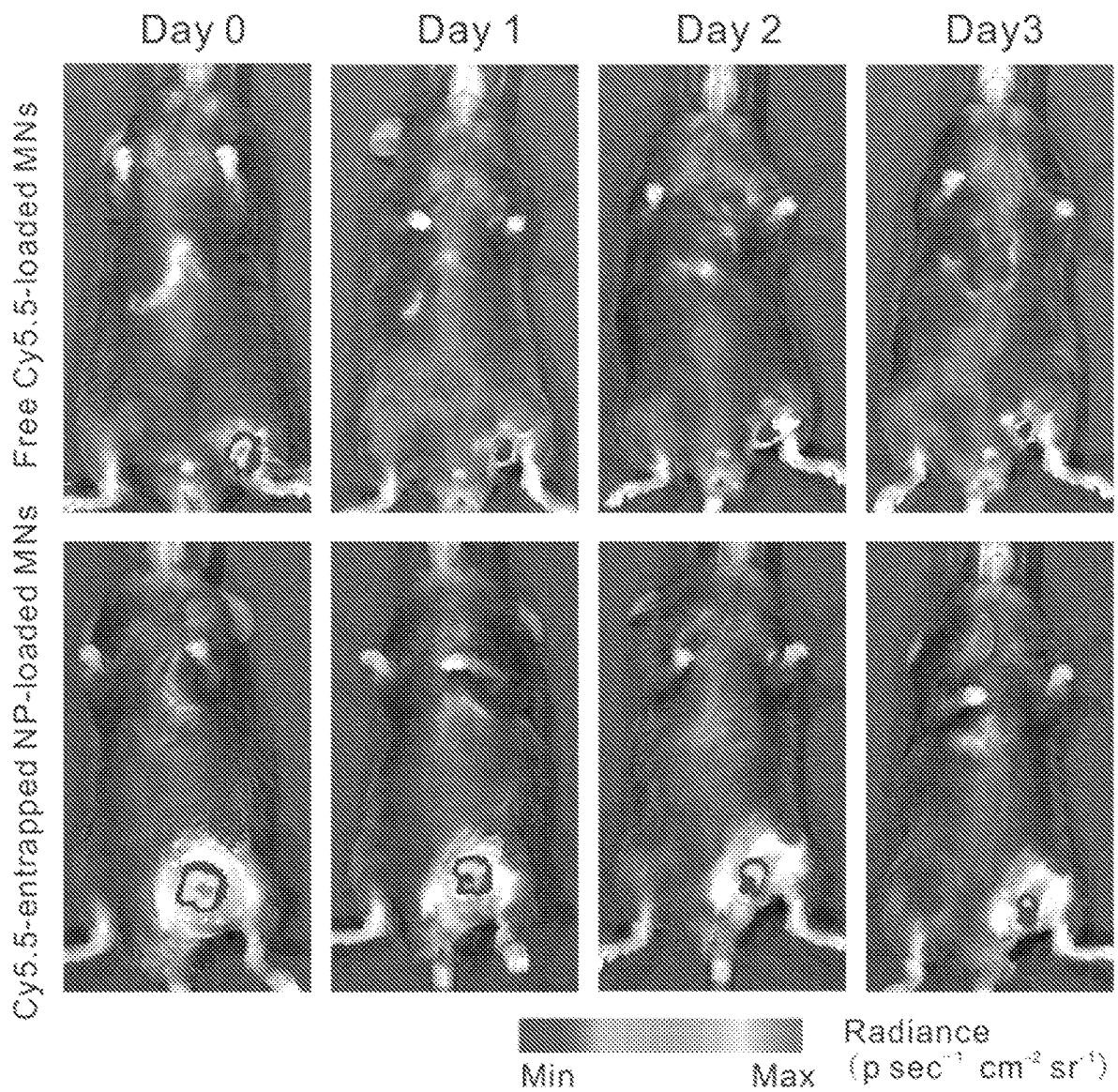
FIG. 10 shows an image of in vivo fluorescence of MN-treated mice at different time points. The fluorescent signal showed the MN patch loaded with free Cy5.5 (upper panel) or Cy5.5-entrapped NPs (lower panel).

The in vivo browning efficacy of the system was examined in a mouse model. In addition to Rosi, a second compound, CL 316243, a β3-adrenergic receptor agonist, was used in dextran NPs and loaded in MNs. CL 316243 is a potent thermogenic activator but works through a distinct mechanism from Rosi. CL 316243 stimulates G protein Gas to activate adenylate cyclase, and consequently causes accumulation of cyclic adenosine monophosphate (cAMP), which leads to thermogenesis and lipolysis. By including this distinctive browning agent, the applicability of the NP system was compared to other drugs. Specifically, wide-type C57BJ/6 mice were randomly divided into three groups (n=6) and treated with the empty vehicle MN (EV) made of only crosslinked m-HA, the HA MN encapsulating Rosi NPs (10 mg/kg body weight (bw)) (Rosi), and the CL 316243 NP-loaded MN (1 mg/kg bw) (CL) at inguinal WAT. MNs penetrated the mouse skin at the inguinal site efficiently, as shown by trypan blue staining of MN-treated tissue (FIG. 2k). MN penetration into the skin exposed the MN tips to the inguinal adipose tissue and successfully delivered model drugs into adipocytes, as shown by fluorescence microscopy (FIG. 8). In vivo fluorescence imaging of Cy5.5-labelled non-degradable NPs without GOx loaded MNs verified that NPs were well restricted in the treated skin region during the whole treatment (FIG. 9). An SEM of the MN revealed the collapsed tips after application, further showing complete release of drug (FIG. 2j). The in vivo sustained release within 3 days was also confirmed by in vivo fluorescence imaging. Compared to the rapid release of free Cy5.5-loaded MN patch, the degradable NPs-loaded patch showed excellent sustained release capability (FIG. 10). Mice were treated with MN patches every three days. Six days post-treatment, mice were sacrificed and the inguinal adipose tissues were collected for histological and gene analysis. The hematoxylin and eosin (H&E) staining of inguinal WAT depicted shrinkage of unilocular white adipocytes and appearance of paucilocular adipocytes, the typical morphology of beige adipocyte, in Rosi MN and CL 316243 MN treated groups, particularly the latter (FIG. 3a). Gene expression analyses further showed browning transformation of inguinal WAT by MN delivery of browning agents (FIG. 3b). The representative brown adipocyte genes including Ucp1, Dio2, Elovl3, Cidea, Pgc-1α, Cox7a1, Cox8b, which are involved in mitochondrial activity and lipid utilization, were up-regulated in both groups, while the inflammatory gene IL-6 tended to be down-regulated. Interestingly, the pan-adipocyte marker Adiponectin was not affected, showing a selective regulation on browning. Notably, the canonical PPARγ target aP2 was up-regulated by Rosi MN but not by CL 316243 MN, showing their distinct browning mechanisms.

Figure 4A:
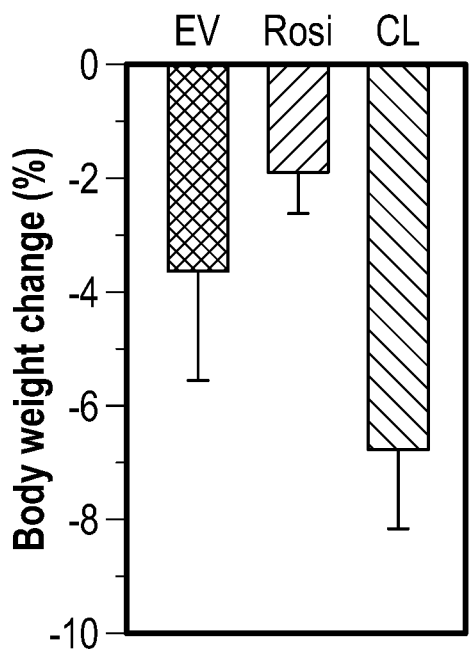
FIGS. 4A-4G show a set of bar charts and line graphs depicting indirect calorimetric analysis of healthy mice treated with HA empty MN patch (EV), Rosi NP-loaded MN patch (Rosi), or CL 316243 NP-loaded MN patch (CL).
Figure 4B:
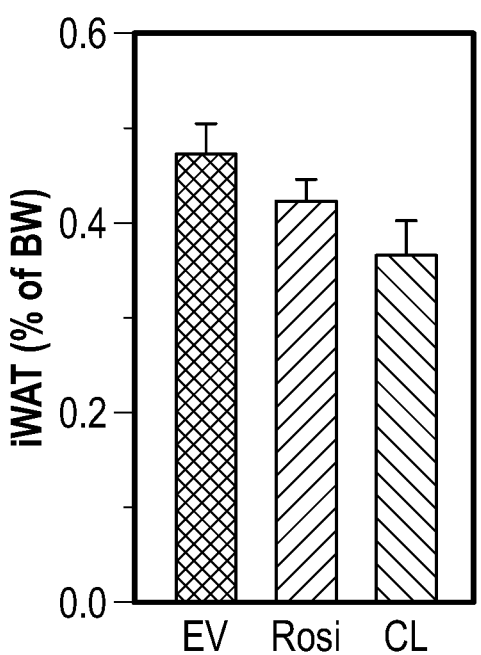
Figure 4C:
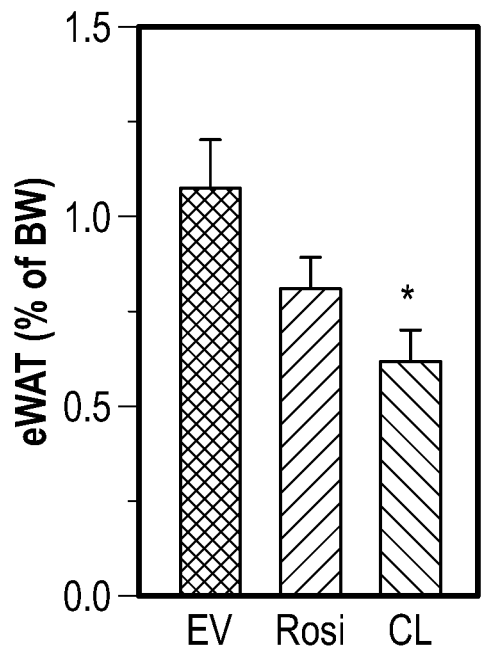
Figure 4D:
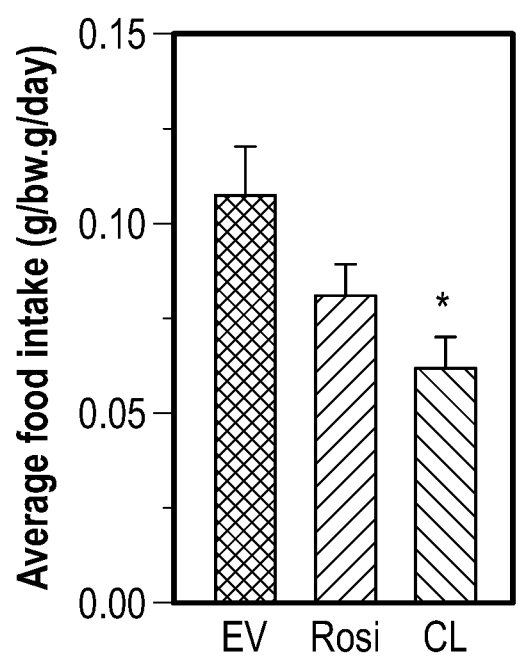
Figure 4E:
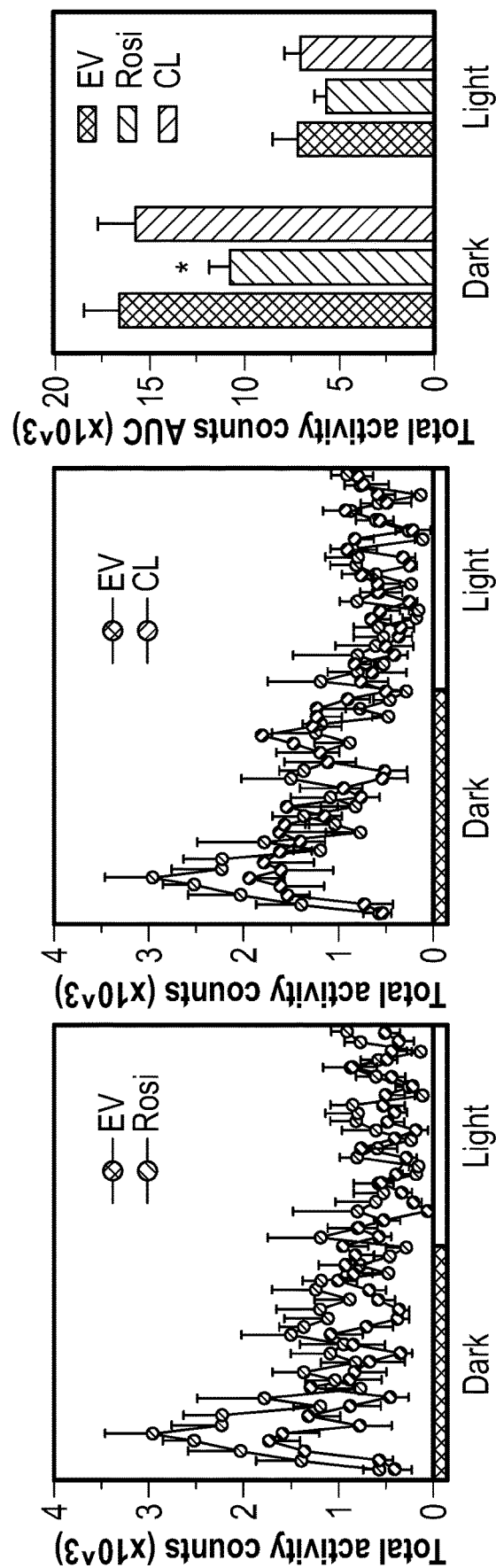
Figure 4F:
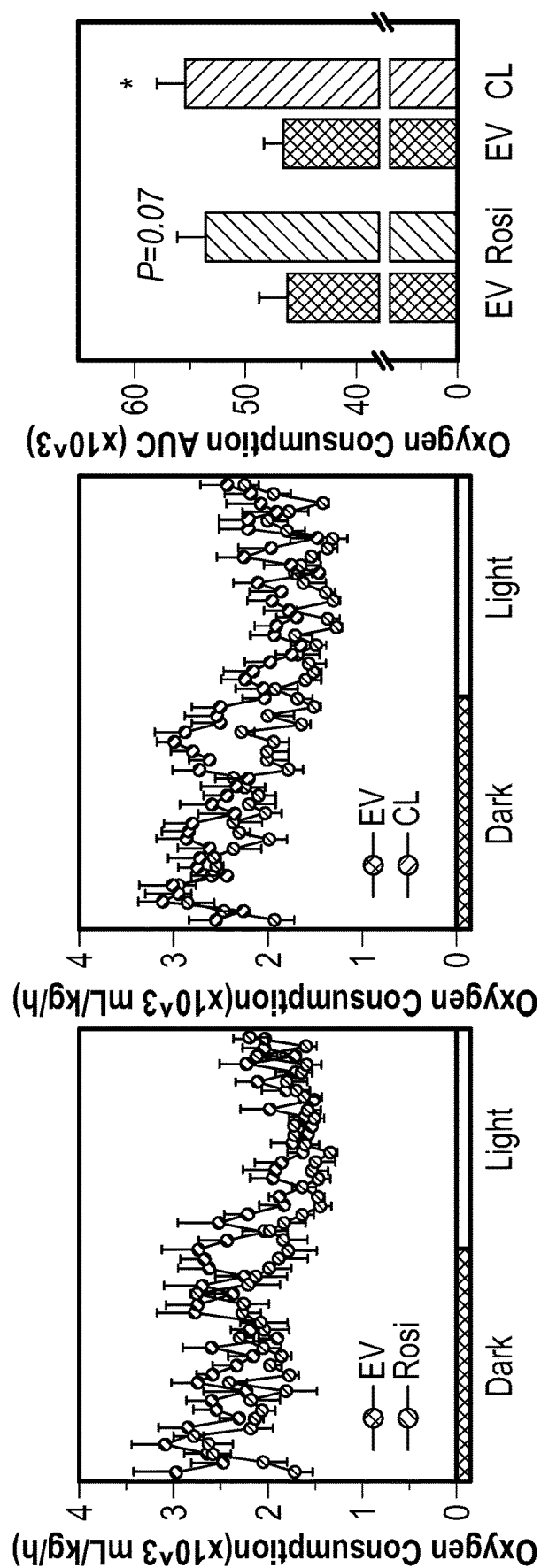
Figure 4G:
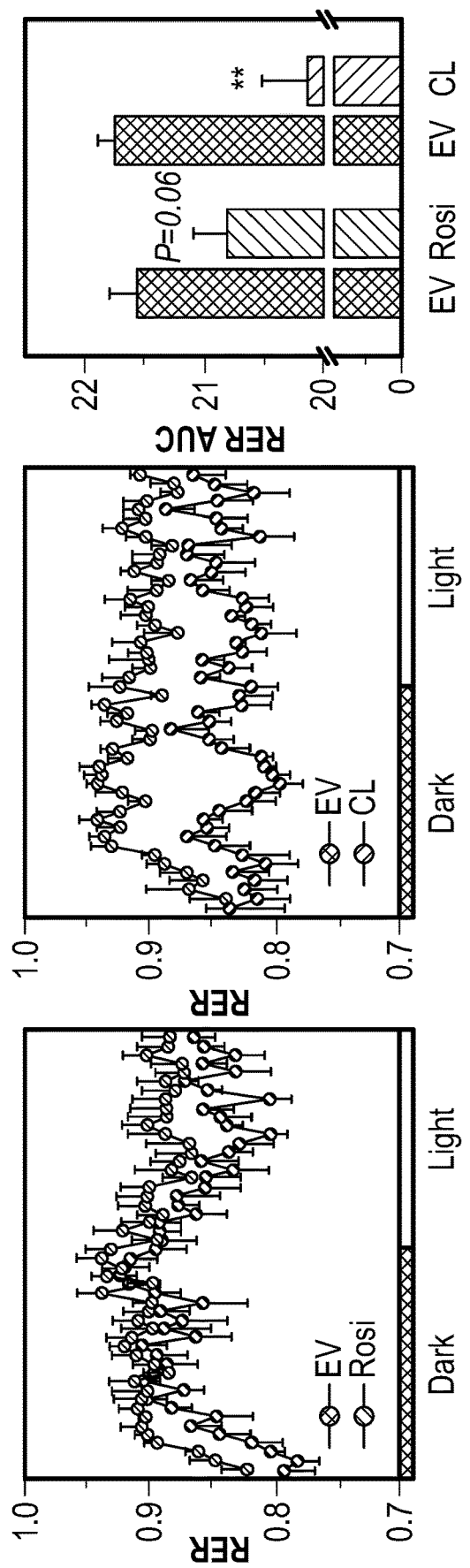

After establishing the feasibility of the MN approach to induce browning in vivo, the browning effects of Rosi MN and CL 316243 MN were tested for lasting and physiological significance. To this end, Rosi MN- or CL 316243 MN-treated mice together with vehicle MN-treated control mice were exposed to indirect calorimetric analysis to measure their systemic metabolic response. All three groups of mice lost weight during the experiment due to the stress of single-housing, but the CL 316243 MN group tended to lose more weight (FIG. 4a). Increased body weight loss of the CL 316243 MN group arose from reduced fat mass, particularly visceral epididymal WAT (eWAT) (FIG. 4b, c). Changes in energy homeostasis were merely caused by energy expenditure, since neither Rosi MN nor CL 316243 affected calorie intake (FIG. 4d). Strikingly, both treatments increased oxygen consumption (FIG. 4e) as an outcome from induced browning (FIG. 3). Unlike CL 316243 MN, Rosi MN reduced locomotor activity during the dark cycle when mice are more active (FIG. 4f), in line with the distinct browning mechanisms of the two drugs. Furthermore, both Rosi and CL 316243 decreased respiration exchange ratio (RER) (FIG. 4g), as shown by released $CO_2$/consumed $O_2$, demonstrating the preference for fatty acid utilization after browning, since only 75% oxygen is needed to fully oxidize carbohydrates compared to fatty acids (3:4 ratio). Taken together, the calorimetric studies show that MN delivery of Rosi or CL 316243 browning agents is an efficient way to induce browning and improve metabolism.

In Vivo Studies of the MNs on Diet-Induced Obese Mice.

Figure 5A:
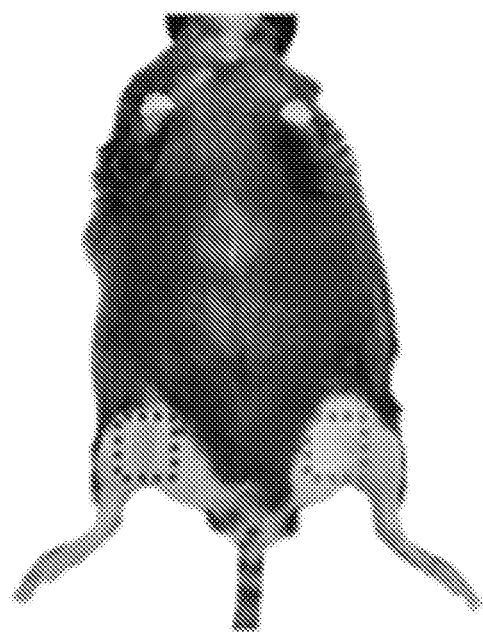
FIGS. 5A-5J show set of photographs, line graphs, micrographs, and bar charts depicting in vivo anti-obesity and anti-diabetic effects of MN patches in an HFD-induced obese mouse model.
Figure 5B:
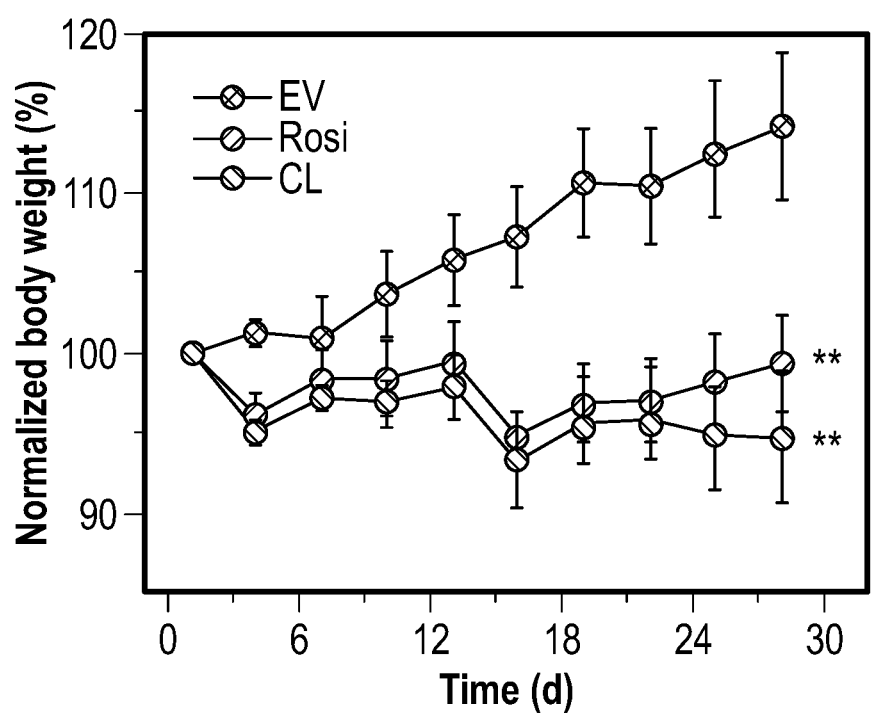
Figure 5C:
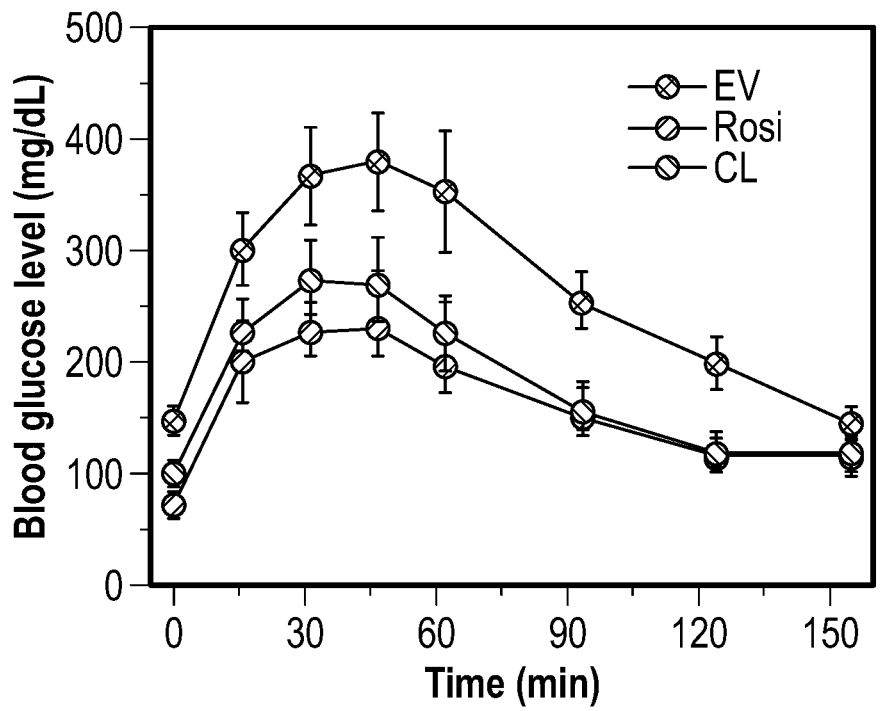
Figure 5D:
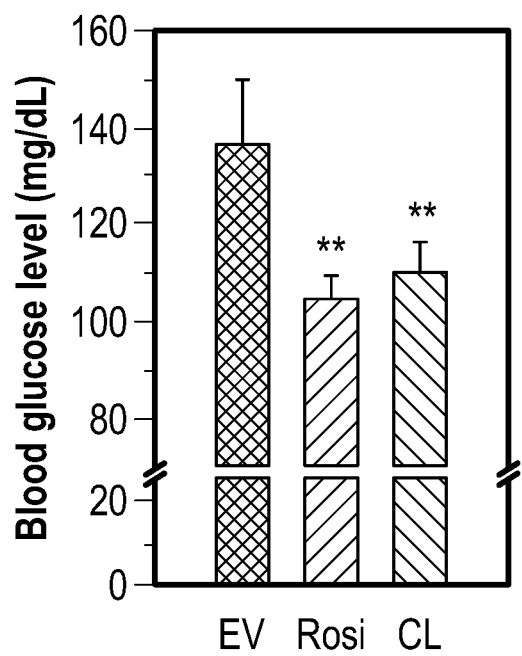
Figure 5E:
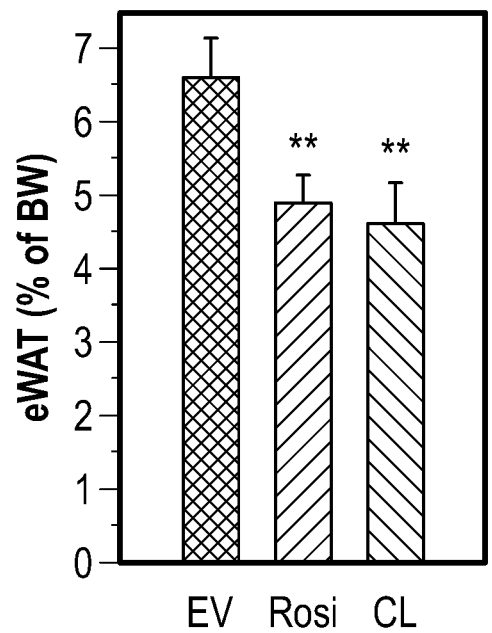
Figure 5F:
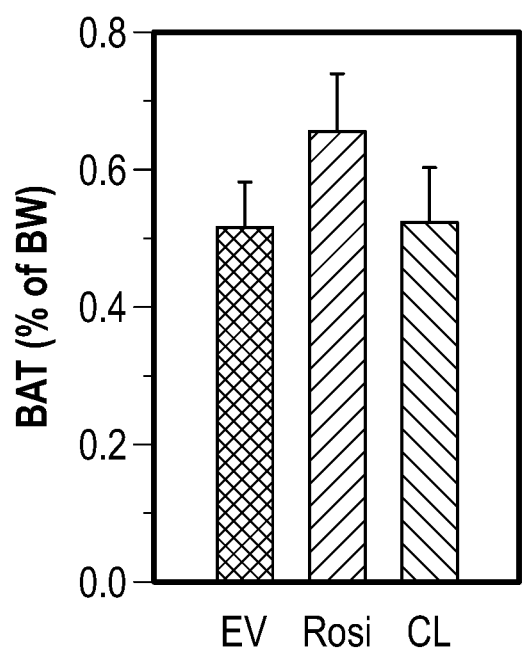
Figure 5G:
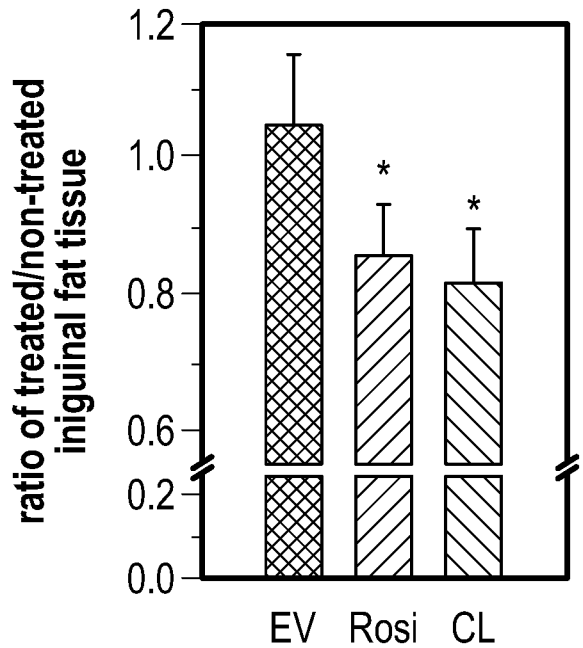
Figure 5H:
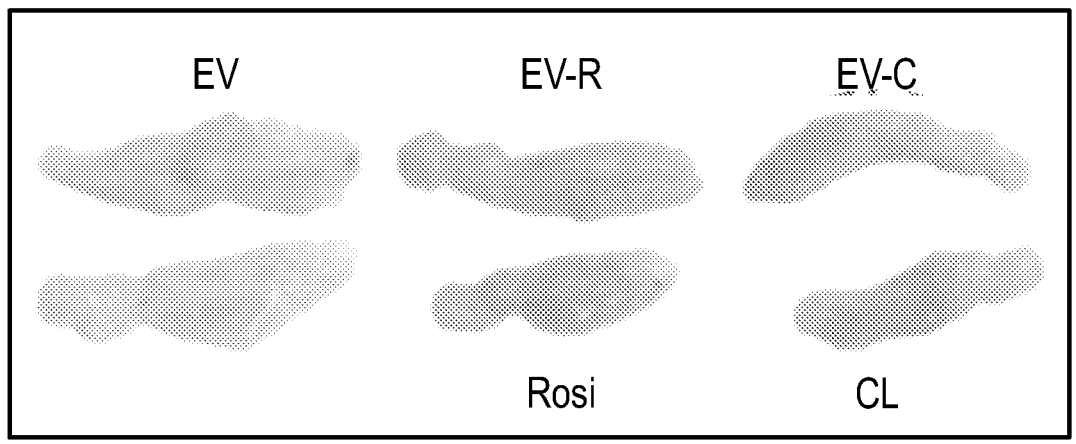
Figure 5I:
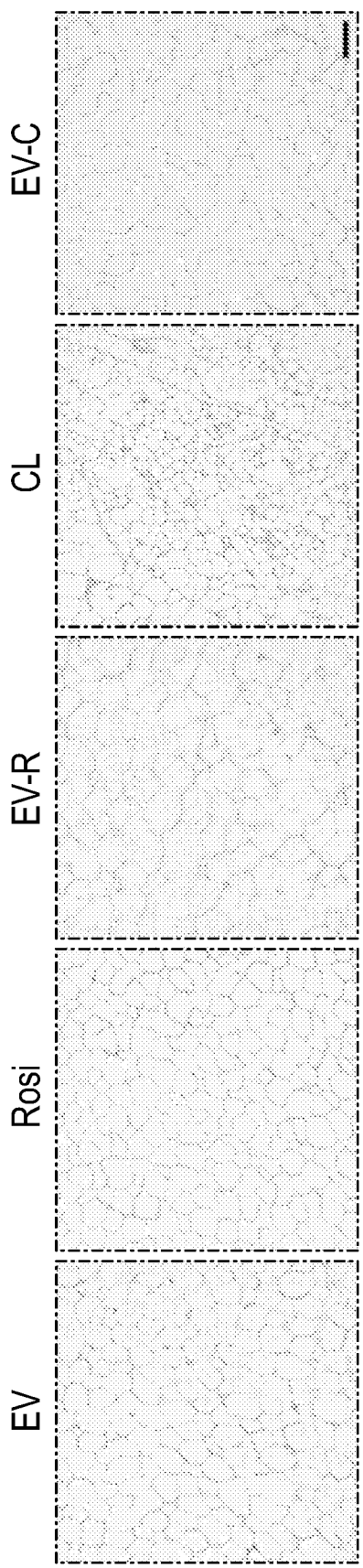
Figure 5J:
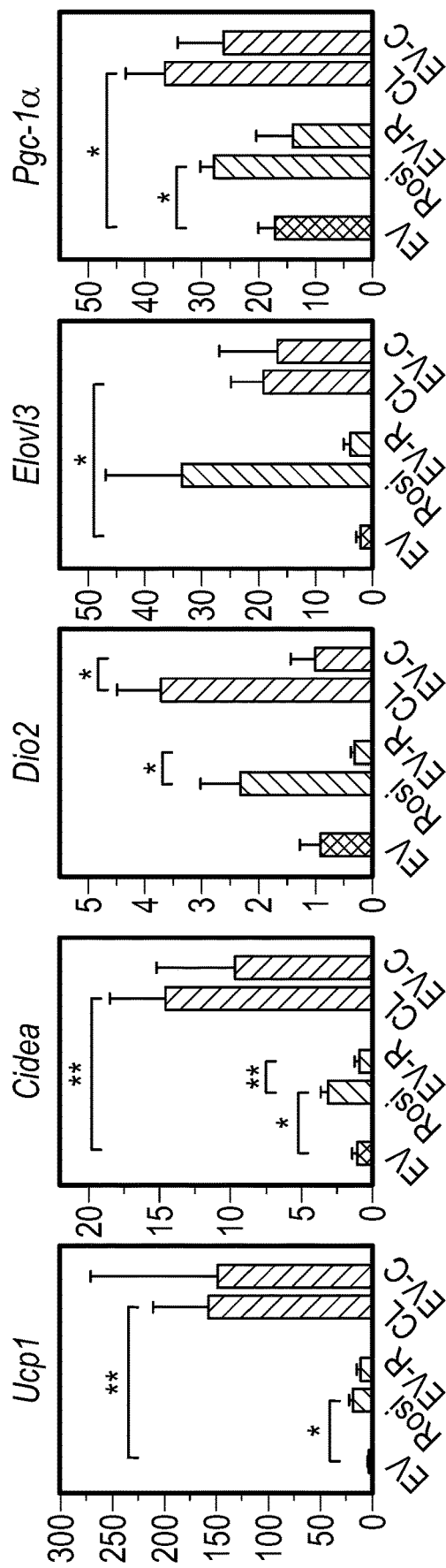
Figure 5J:
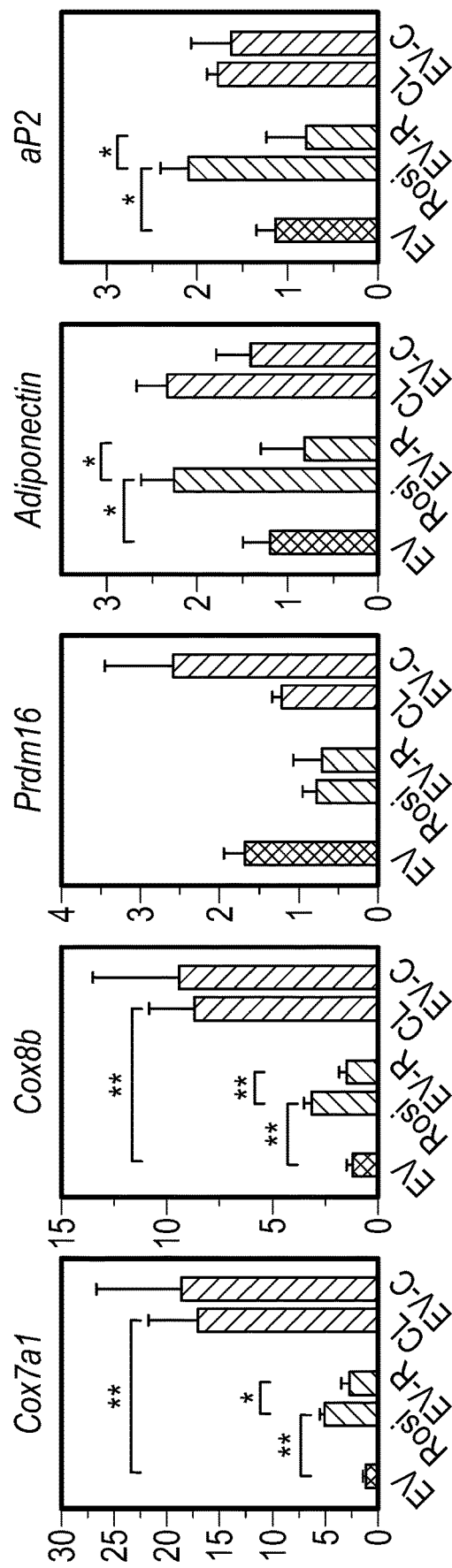
Figure 11:
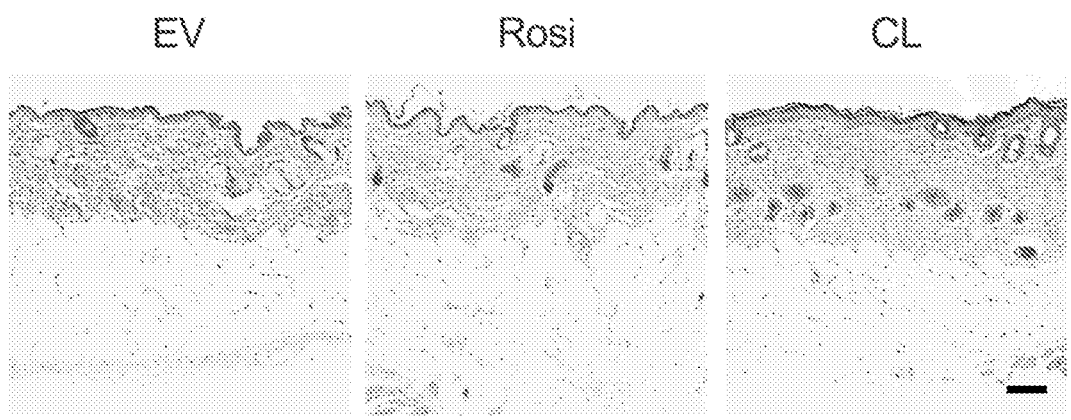
FIG. 11 shows a micrograph of H&E-stained skin sections administered empty, Rosi NP-loaded, and CL 316243 NP-loaded MNs (from left to right) with surrounding tissues after one month of treatment (scale bar: 100 µm).

The physiological effects of MN browning agent patches were striking and encouraging. Thus, the therapeutic potential of MNs in obese mice was evaluated. In high-fat diet (HFD)-induced obesity C57BL/6 mice, a MN browning agent patch was applied to one side inguinal region (Rosi or CL) and an empty HA MN was applied to the other side as vehicle control (EV-R and EV-C) (FIG. 5a). For control mice, both sides were treated with empty HA MN (EV). Rosi is a potent insulin sensitizer but also causes weight gain. Surprisingly, MN delivery of Rosi also prevented weight gain similar to CL 316243 MN, resulting in a ~15% inhibition at the end of the four-week treatment (FIG. 5b). Both Rosi MN and CL 316243 MN efficiently improved glucose clearance rate after injecting mice with a bolus of glucose in intraperitoneal glucose tolerance testing (IPGTT) (FIG. 5c), and decreased fasting blood glucose levels (the diagnostic indicator of diabetes) from 140 mg/dL in control mice to ~110 mg/dL (FIG. 5d), indicating an improvement of insulin sensitivity. Intriguingly, this improvement in insulin sensitivity was caused by browning rather than by the insulin sensitizing function of Rosi itself, since CL 316243 showed the same effect. As a consequence of increased browning and lipid utilization shown in FIG. 4, a ~30% reduction of eWAT (FIG. 5e) but not in the classic interscapular BAT (FIG. 5f) was observed. More importantly, MN delivery of browning agents reduced inguinal fat pad locally. The sizes of treated sides, either by Rosi MN or CL 316243 MN, were reduced compared to untreated sides (EV-R or EV-C) (FIG. 5g, h). H&E stained sections showed smaller adipocytes in inguinal WAT only in the mice administered with drug-containing patches, but no obvious browning was observed at the other site administered with empty control patches (FIG. 5i). Brown adipocyte genes were more highly induced in the treated side, particularly by Rosi MN (FIG. 5j), showing a restricted browning effect of MN patches. The gene Adiponectin was up-regulated in both Rosi MN and CL 316243 MN treated sites (FIG. 5j), showing improved adipose health. The PPARγ downstream target aP2 was induced only by MN Rosi (FIG. 5j), further showing a local effect of the MN patch. H&E stained histological images of mouse skin surrounding MN-treated areas after one-month administration showed insignificant lesions in the skin, demonstrating excellent biocompatibility of the MN patches (FIG. 11).

Conclusions

Disclosed herein is a technique based on a NP-integrated microneedle patch that facilitates local browning of WAT. The degradable NPs released browning agents into the subcutaneous region in the presence of glucose and facilitated transformation of WAT towards brown-like adipose tissue. Importantly, MNs restricted browning agents to the treated region and thus minimize potential side effects on other organs of systemically (e.g. orally or intravenously) administered browning agents. In vivo data further demonstrated systemically increased energy expenditure and fatty acid oxidation, effective body weight control in diet-induced obese mice, and improved insulin sensitivity. Taken together, provided herein is an alternative strategy in administering drugs through MN as potential therapeutics for clinical treatment of obesity and its comorbidities such as type-2 diabetes.

Methods

Materials.

All chemicals were purchased from Sigma-Aldrich unless otherwise specified and were used as received. Rosiglitazone was ordered from Abcam (Cambridge, Mass., USA). CL 316243 was purchased from Cayman Chemical (Ann Arbor, Mich., USA). Deionized water was prepared by a Millipore NanoPure purification system (resistivity higher than 18.2 MΩ $cm^{-1}$).

Preparation of Rosiglitazone-Loaded Dextran Nanoparticles.

Dextran nanoparticles (NPs) were prepared by an improved double emulsion method. Briefly, 5 mL dichloromethane (DCM) containing 200 mg of m-dextran and 20 mg rosiglitazone (Rosi) were emulsified with 0.5 mL of aqueous solution containing 3.5 mg of enzymes (weight ratio of glucose oxidase to catalase 4:1) by sonication for 45 cycles (1 s each with a duty of 40%). The resulting primary solution was further poured into 25 mL 1% alginate aqueous solution (Mv=1.6×$10^5$ Da) for another 45-cycle sonication. The double emulsion was immediately transferred into 150 mL 0.2% alginate and stirred at room temperature for 2 h to evaporate DCM. Afterwards, nanoparticles were collected by centrifugation at 10,000 rpm and washed by distilled water three times. The loading capacity (LC) and encapsulation efficiency (EE) of Rosi were determined by measuring UV-Vis absorption of released Rosi from nanoparticles using a Nanodrop 2000C spectrometer (Thermo Scientific) at absorbance 317 nm. LC and EE were calculated as LC=B/C, EE=B/A, where A was the expected encapsulated amount of Rosi, B was the encapsulated amount of Rosi, and C was the total weight of the particles. Particle size and polydispersity intensity were measured by dynamic light scattering (DLS). The zeta potential of NPs was determined by their electrophoretic mobility using the same instrument after appropriate dilution in DI water. Measurements were made in triplicate at room temperature. NPs morphology was investigated by a FEI Verios 460L field-emission scanning electron microscope (FESEM).

In Vitro Release Studies.

The in vitro release profile of Rosi from dextran nanoparticles was evaluated through incubation of nanoparticles in 1 mL PBS buffer (NaCl, 137 mM; KCl, 2.7 mM; $Na_2HPO_4$, 10 mM; $KH_2PO_4$, 2 mM; pH 7.4) at 37° C. on an orbital shaker, to which 100 mg/dL glucose was added to reach normoglycemic level in human body. At predetermined time points, the sample was centrifuged (10,000 rpm, 1 min) and 10 μL the supernatant was taken out for analysis by measuring the UV-Vis absorbance at 317 nm using a Nanodrop 2000C spectrometer.

Fabrication of Browning Agent Microneedle (MN) Patch.

Each MN was fabricated using the uniform silicone molds from Blueacre Technology Ltd. Each needle had a 300 μm by 300 μm round base tapering to a height of 800 μm. Needles were arranged in an 11×11 array with 600 μm tip-to-tip spacing. To fabricate nanoparticles-loaded microneedles, the prepared nanoparticle suspension was first deposited by pipet onto the MN mold surface (30 μL/array). Then, molds were placed under vacuum (600 mmHg) for 5 min to allow the solution filled the MN cavities. Afterwards, the covered molds were centrifuged using a Hettich Universal 32R centrifuge for 10 min at 2,000 rpm. Finally, 3 mL premixed N,N'-methylenebisacrylamide (MBA, w/v: 2%), photoinitiator (Irgacure 2959, w/v: 0.5%) and m-HA solution (w/v: 4%) were added into the prepared micromold reservoir and allowed to dry at 20° C. under vacuum desiccator. m-HA was synthesized following a previous reported method. After complete desiccation, the MN patch was carefully detached from the silicone mold and underwent crosslinking polymerization via UV irradiation (wavelength: 365 nm at an intensity of 9 mW/cm²) for 30 s. The resulting MN-array patches were stored in a sealed six well container. Morphology of MNs was characterized via a FEI Verios 460L field-emission scanning electron microscope (FESEM).

In Vivo Browning Studies in Lean Mice.

8-week old male C57BL/6 mice ordered from Charles River (Raleigh, N.C., USA) or the Jackson Laboratory were used. The animal study protocols were approved by the Institutional Animal Care and Use Committee at North Carolina State University and University of North Carolina at Chapel Hill, or by the Columbia University Animal Care and Utilization Committee. Mice were caged at 22±1° C. with free access to water and regular chow diet on a 12 h light/dark cycle. Mice were given least one-week adaption before experiments. Three groups of animals (n=6) were treated with empty hyaluronic acid (HA) MN patch (EV), Rosi NP-loaded MN patch (10 mg/kg) (Rosi), or CL316243 NP-loaded MN patch (1 mg/kg) (CL) on inguinal regions every three days. For indirect calorimetric studies, mice were subjected to the Comprehensive Lab Animal Monitoring System (CLAMS). Metabolic activities were monitored during treatment, including oxygen consumption, food intake, locomotor activity and body weight. Six days post-administration, animals were sacrificed and inguinal adipose tissues were collected for histological and RNA analysis. Interscapular browning adipose tissues (BAT) and epididymal white adipose tissues (WAT) were weighted.

Browning MN Patch Treatments on Diet Induced Obesity (DIO) Mice.

Male C57BL/6 mice were fed a high-fat diet (HFD; 60% kcal from fat) for 8 weeks to induce obesity and insulin resistance. Three groups of five mice each were treated with empty HA, Rosi (10 mg/kg), or CL316243 (1 mg/kg) through a transdermal patch on one side of the inguinal areas under isoflurane anesthesia. The other side of inguinal tissue of each mouse was treated with an empty HA microneedle patch. Each patch was changed every 3 days for 4 weeks. Body weight was monitored during the treatment period. The glucose tolerance test was performed in mice 3-weeks post-treatment. Mice fasted for 16 h (overnight) before glucose administration. Mice were intraperitoneal injected with glucose (2 g/kg diluted in PBS) and blood glucose levels were monitored over time. At the end of 4-weeks of MN treatment, mice were euthanized by $CO_2$ asphyxiation, and adipose tissues (inguinal WAT, epididymal WAT, and interscapular BAT) were collected for analyses. The skin tissues around the treated areas were also collected for biocompatibility evaluation of MN patches.

Synthesis of Pendant Acetal-Modified Dextran (m-Dextran).

1.0 g of dextran (Mn=9~11 kDa) was added to a flame-dried round-bottom flask and purged with nitrogen. 10 mL of anhydrous dimethyl sulfoxide (DMSO) was added to the flask and stirred until complete dissolution of the dextran. Pyridinium p-toluenesulfonate (PPTS, 15.6 mg, 0.062 mmol) was added to the solution followed by the addition of 2-ethoxypropene (4.16 mL, 37 mmol). The reaction mixture was purged with nitrogen and sealed with parafilm to prevent reactant evaporation. The reaction was stirred at room temperature for 30 min, and then quenched by the addition of 1 mL of triethylamine. The mixture was then precipitated and washed three times in basic water (pH~8) to prevent undesired degradation and collected by centrifugation at 8,000 rpm for 15 min. The product was lyophilized to obtain white solid. 1H NMR (DMSO-$d_6$, 300 MHz, δ ppm): 1.10 (m, $OCH_2CH_3$), 1.30 (m, $C(CH_3)_2$), 3.40 (m, $OCH_2CH_3$), 3.55-3.85 (br, dextran $C_2$—H~$C_6$—H), 4.88 (br, dextran $C_1$—H)

Mechanical Strength Test.

Mechanical strength of MNs was measured by pressing MNs against a stainless-steel plate. The speed of the top stainless-steel plate movement towards the MN-array patch was 1 μm/s.

Skin Penetration Efficiency Test.

After administering the MN-array on skin at the inguinal site, mice were euthanized by $CO_2$ asphyxiation, and skin was excited and stained with trypan blue for imaging by optical microscopy (Leica EZ4 D stereo microscope). To evaluate the biocompatibility of the MN-array patches, the tissue samples were fixed in 10% formalin for 18 h and then embedded in paraffin, cut into 50 μm sections, and stained using hematoxylin and eosin (H&E) for histological analysis.

RNA Analysis.

RNA was extracted from tissues or cells by combining TriZol reagent and NucleoSpin RNA kit with DNase I digestion (Macherey-Nagel), following the manufacturer's instructions. 1 μg total RNA was used to synthesize cDNA by using the High-capacity cDNA Reverse Transcription kit (Applied Biosystems). Quantitative real-time PCR (Q-PCR) were performed on a Bio-Rad CFX96 Real-Time PCR platform by using the GoTaq qPCR Master Mix (Promega). Relative gene expressions were calculated by using ΔΔCt method with Cyclophilin A (cultured cells) or RPL23 (tissues) as the reference gene. Primer sequences are listed in Table 1.

TABLE 1

List of Q-PCR DNA Primer sequences.

| Gene | Q-PCR Primer sequence | Sequence ID NO: |
|---|---|---|
| Adipsin | Forward: CATGCTCGGCCCTACATGG | SEQ ID NO: 1 |
|  | Reverse: CACAGAGTCGTCATCCGTCAC | SEQ ID NO: 2 |
| Adiponectin | Forward: GCACTGGCAAGTTCTACTGCAA | SEQ ID NO: 3 |
|  | Reverse: GTAGGTGAAGAGAACGGCCTTGT | SEQ ID NO: 4 |
| aP2 | Forward: ACACCGAGATTTCCTTCAAACTG | SEQ ID NO: 5 |
|  | Reverse: CCATCTAGGGTTATGATGCTCTTCA | SEQ ID NO: 6 |
| Cidea | Forward: TGCTCTTCTGTATCGCCCAGT | SEQ ID NO: 7 |
|  | Reverse: GCCGTGTTAAGGAATCTGCTG | SEQ ID NO: 8 |
| Cox7a1 | Forward: CAGCGTCATGGTCAGTCTGT | SEQ ID NO: 9 |
|  | Reverse: AGAAAACCGTGTGGCAGAGA | SEQ ID NO: 10 |
| Cox8b | Forward: GAACCATGAAGCCAACGACT | SEQ ID NO: 11 |
|  | Reverse: GCGAAGTTCACAGTGGTTCC | SEQ ID NO: 12 |
| Cyclophilin A | Forward: TATCTGCACTGCCAAGACTGAGTG | SEQ ID NO: 13 |
|  | Reverse: CTTCTTGCTGGTCTTGCCATTCC | SEQ ID NO: 14 |
| Dio2 | Forward: AGAGTGGAGGCGCATGCT | SEQ ID NO: 15 |
|  | Reverse: GGCATCTAGGAGGAAGCTGTTC | SEQ ID NO: 16 |
| Elovl3 | Forward: CCAACAACGATGAGCAACAG | SEQ ID NO: 17 |
|  | Reverse: CGGGTTAAAAATGGACCTGA | SEQ ID NO: 18 |
| IL-6 | Forward: TTCCATCCAGTTGCCTTCTT | SEQ ID NO: 19 |
|  | Reverse: ATTTCCACGATTTCCCAGAG | SEQ ID NO: 20 |
| Perilipin | Forward: GGCCTGGACGACAAAACC | SEQ ID NO: 21 |
|  | Reverse: CAGGATGGGCTCCATGAC | SEQ ID NO: 22 |
| Pgc-1α | Forward: CCCTGCCATTGTTAAGACC | SEQ ID NO: 23 |
|  | Reverse: TGCTGCTGTTCCTGTTTTC | SEQ ID NO: 24 |
| Pparγ1 | Forward: AGAAGCGGTGAACCACTGAT | SEQ ID NO: 25 |
|  | Reverse: GAATGCGAGTGGTCTTCCAT | SEQ ID NO: 26 |
| Pparγ2 | Forward: TCTGGGAGATTCTCCTGTTGA | SEQ ID NO: 27 |
|  | Reverse: GGTGGGCCAGAATGGCATCT | SEQ ID NO: 28 |
| Prdm16 | Forward: TGGCCTTCATCACCTCTCTGAA | SEQ ID NO: 29 |
|  | Reverse: TTTCTGATCCACGGCTCCTGTGA | SEQ ID NO: 30 |
| Resistin | Forward: AAGAACCTTTCATTTCCCCTCCT | SEQ ID NO: 31 |
|  | Reverse: GTCCAGCAATTTAAGCCAATGTT | SEQ ID NO: 32 |
| Rpl23 | Forward: TGTCGAATTACCACTGCTGG | SEQ ID NO: 33 |
|  | Reverse: CTGTGAAGGGAATCAAGGGA | SEQ ID NO: 34 |
| Ucp1 | Forward: ACTGCCACACCTCCAGTCATT | SEQ ID NO: 35 |
|  | Reverse: CTTTGCCTCACTCAGGATTGG | SEQ ID NO: 36 |

Statistical Analysis.

All results are presented as Mean±SEM or Mean±SD. Statistical analysis was performed using Student's t-test. With a p value <0.05, the differences between experimental groups and control groups were considered statistically significant.

REFERENCES

Au-Yong, I. T.; Thom, N.; Ganatra, R.; Perkins, A. C.; Symonds, M. E. Brown Adipose Tissue and Seasonal Variation in Humans. Diabetes 2009, 58, 2583-2587.

Bakopanos, E.; Silva, J. E. Thiazolidinediones Inhibit the Expression of Beta3-Adrenergic Receptors at a Transcriptional Level. Diabetes 2000, 49, 2108-2115.

Bartelt, A.; Heeren, J. Adipose Tissue Browning and Metabolic Health. Nat. Rev. Endocrinol. 2014, 10, 24-36.

Bonet, M. L.; Oliver, P.; Palou, A. Pharmacological and Nutritional Agents Promoting Browning of White Adipose Tissue. Biochim Biophys. Acta, Mol. Cell. Biol. Lipids 2013, 1831, 969-985.

Cai, X.; Jia, X.; Gao, W.; Zhang, K.; Ma, M.; Wang, S.; Zheng, Y.; Shi, J.; Chen, H. A Versatile Nanotheranostic Agent for Efficient Dual-Mode Imaging Guided Synergistic Chemo-Thermal Tumor Therapy. Adv. Funct. Mater. 2015, 25, 2520-2529.

Chang, S.-H.; Stoll, C. R.; Song, J.; Varela, J. E.; Eagon, C. J.; Colditz, G. A. The Effectiveness and Risks of Bariatric Surgery: an Updated Systematic Review and Meta-Analysis, 2003-2012. JAMA Surg. 2014, 149, 275-287.

Cipolletta, D.; Feuerer, M.; Li, A.; Kamei, N.; Lee, J.; Shoelson, S. E.; Benoist, C.; Mathis, D. PPARγ is a Major Driver of the Accumulation and Phenotype of Adipose Tissue Treg Cells. Nature 2012, 486, 549-553.

Clapham, J. C.; Arch, J. R.; Tadayyon, M. Anti-Obesity Drugs: a Critical Review of Current Therapies and Future Opportunities. Pharmacol. Ther. 2001, 89, 81-121.

Colman, E.; Golden, J.; Roberts, M.; Egan, A.; Weaver, J.; Rosebraugh, C. The FDA's Assessment of Two Drugs for Chronic Weight Management. New Engl. J. Med. 2012, 367, 1577-1579.

Dietrich, M. O.; Horvath, T. L. Limitations in Anti-Obesity Drug Development: the Critical Role of Hunger-Promoting Neurons. Nat. Rev. Drug Discov. 2012, 11, 675-691.

Friedman, J. M. Obesity: Causes and Control of Excess Body Fat. Nature 2009, 459, 340-342.

Gu, Z.; Aimetti, A. A.; Wang, Q.; Dang, T. T.; Zhang, Y; Veiseh, O.; Cheng, H.; Langer, R. S.; Anderson, D. G. Injectable Nano-Network for Glucose-Mediated Insulin Delivery. ACS Nano 2013, 7, 4194-4201.

Harms, M.; Seale, P. Brown and Beige Fat: Development, Function and Therapeutic Potential. Nat. Med. 2013, 19, 1252-1263.

Heymsfield, S. B.; Wadden, T. A. Mechanisms, Pathophysiology, and Management of Obesity. New Engl. J. Med. 2017, 376, 254-266.

Jiang, T.; Mo, R.; Bellotti, A.; Zhou, J.; Gu, Z. Gel-Liposome-Mediated Co-Delivery of Anticancer Membrane-Associated Proteins and Small-Molecule Drugs for Enhanced Therapeutic Efficacy. Adv. Funct. Mater. 2014, 24, 2295-2304.

Kajimura, S.; Spiegelman, B. M.; Seale, P. Brown and Beige Fat: Physiological Roles Beyond Heat Generation. Cell Metab. 2015, 22, 546-559.

Kalliokoski, O.; Jacobsen, K. R.; Darusman, H. S.; Henriksen, T.; Weimann, A.; Poulsen, H. E.; Hau, J.; Abelson, K. S. Mice Do Not Habituate to Metabolism Cage Housing—a Three Week Study of Male BALB/c Mice. PLoS One 2013, 8, e58460.

Klein, J.; Fasshauer, M.; Ito, M.; Lowell, B. B.; Benito, M.; Kahn, C. R. β3-Adrenergic Stimulation Differentially Inhibits Insulin Signaling and Decreases Insulin-Induced Glucose Uptake in Brown Adipocytes. J. Biol. Chem. 1999, 274, 34795-34802.

Kogan, G.; Šoltés, L.; Stern, R.; Gemeiner, P. Hyaluronic Acid: a Natural Biopolymer with a Broad Range of Biomedical and Industrial Applications. Biotechnol. Lett. 2007, 29, 17-25.

Li, D.; Zhang, F.; Zhang, X.; Xue, C.; Namwanje, M.; Fan, L.; Reilly, M. P.; Hu, F.; Qiang, L. Distinct Functions of PPARγ Isoforms in Regulating Adipocyte Plasticity. Biochem. Biophys. Res. Commun. 2016, 481, 132-138.

Lowell, M., PhD, BB; Flier, M., J S. Brown Adipose Tissue, β3-Adrenergic Receptors, and Obesity. Annu. Rev. Med. 1997, 48, 307-316.

Lu, Y; Aimetti, A. A.; Langer, R.; Gu, Z. Bioresponsive Materials. Nat. Rev. Mater. 2016, 1, 16075.

Mo, R.; Jiang, T.; Di, J.; Tai, W.; Gu, Z. Emerging Micro- and Nanotechnology Based Synthetic Approaches for Insulin Delivery. Chem. Soc. Rev. 2014, 43, 3595-3629.

Nagy, T. R.; Krzywanski, D.; Li, J.; Meleth, S.; Desmond, R. Effect of Group vs. Single Housing on Phenotypic Variance in C57BL/6J Mice. Obesity Res. 2002, 10, 412-415.

Nedergaard, J.; Cannon, B. The Browning of White Adipose Tissue: Some Burning Issues. Cell Metab. 2014, 20, 396-407.

Ogden, C. L.; Carroll, M. D.; Fryar, C. D.; Flegal, K M. Prevalence of Obesity Among Adults and Youth: United States, 2011-2014. NCHS data brief 2015, 219, 1-8. Organization, W. H. Obesity and Overweight. Fact sheet No 311. 2015. Google Scholar 2015.

Prausnitz, M. R.; Langer, R. Transdermal Drug Delivery. Nat. Biotechnol. 2008, 26, 1261-1268.

Rucker, D.; Padwal, R.; Li, S. K.; Curioni, C.; Lau, D. C. Long Term Pharmacotherapy for Obesity and Overweight: Updated Meta-Analysis. BMJ 2007, 335, 1194-9.

Sun, W; Hu, Q.; Ji, W.; Wright, G.; Gu, Z. Leveraging Physiology for Precision Drug Delivery. Physiol. Rev. 2017, 97, 189-225.

Vernochet, C.; Peres, S. B.; Davis, K. E.; McDonald, M. E.; Qiang, L.; Wang, H.; Scherer, P. E.; Farmer, S. R. C/EBPα and the Corepressors CtBP1 and CtBP2 Regulate Repression of Select Visceral White Adipose Genes During Induction of the Brown Phenotype in White Adipocytes by Peroxisome Proliferator-Activated Receptor γ Agonists. Mol. Cell. Biol. 2009, 29, 4714-4728.

Voikar, V.; Polus, A.; Vasar, E.; Rauvala, H. Long-Term Individual Housing in C57BL/6J and DBA/2 Mice: Assessment of Behavioral Consequences. Genes Brain Behav. 2005, 4, 240-252.

Wang, C.; Ye, Y.; Hochu, G. M.; Sadeghifar, H.; Gu, Z. Enhanced Cancer Immunotherapy by Microneedle Patch-Assisted Delivery of Anti-PD1 Antibody. Nano Lett. 2016, 16, 2334-2340.

Weyer, C.; de Souza, C. J. Development of β3-Adrenoceptor Agonists as Antiobesity and Antidiabetes Drugs in Humans: Current Status and Future Prospects. Drug Dev. Res. 2000, 51, 80-93.

Weyer, C.; Gautier, J.; Danforth Jr, E. Development of Beta 3-Adrenoceptor Agonists for the Treatment of Obesity and Diabetes An Update. Diabetes Metab. 1999, 25, 11-21

Whittle, A.; Relat-Pardo, J.; Vidal-Puig, A. Pharmacological Strategies for Targeting BAT Thermogenesis. Trends Pharmacol. Sci. 2013, 34, 347-355.

Wu, J.; Cohen, P.; Spiegelman, B. M. Adaptive Thermogenesis in Adipocytes: Is Beige the New Brown? Genes Dev. 2013, 27, 234-250.

Xue, Y.; Xu, X.; Zhang, X.-Q.; Farokhzad, 0. C.; Langer, R. Preventing Diet-Induced Obesity in Mice by Adipose Tissue Transformation and Angiogenesis Using Targeted Nanoparticles. Proc. Natl. Acad. Sci. U.S.A. 2016, 201603840.

Ye, Y.; Yu, J.; Wang, C.; Nguyen, N. Y; Walker, G. M.; Buse, J. B.; Gu, Z. Microneedles Integrated with Pancreatic Cells and Synthetic Glucose-Signal Amplifiers for Smart Insulin Delivery. Adv. Mater. 2016, 28, 3115-3121.

Yu, J.; Zhang, Y.; Bomba, H.; Gu, Z. Stimuli-Responsive Delivery of Therapeutics for Diabetes Treatment. Bioeng. Transl. Med. 2016, 1, 323-337.

Yu, J.; Zhang, Y.; Ye, Y.; DiSanto, R.; Sun, W.; Ranson, D.; Ligler, F. S.; Buse, J. B.; Gu, Z. Microneedle-Array Patches Loaded with Hypoxia-Sensitive Vesicles Provide Fast Glucose-Responsive Insulin Delivery. Proc. Natl. Acad. Sci. U.S.A. 2015, 112, 8260-8265.

Yu, S.; Gavrilova, O.; Chen, H.; Lee, R.; Liu, J.; Pacak, K.; Parlow, A.; Quon, M. J.; Reitman, M. L.; Weinstein, L. S. Paternal versus Maternal Transmission of a Stimulatory G-Protein a Subunit Knockout Produces Opposite Effects on Energy Metabolism. J. Clin. Invest. 2000, 105, 615-623.

Zhang, Y; Yu, J.; Shen, Q.; Gu, Z. Glucose-Responsive Synthetic Closed-Loop Insulin Delivery Systems. Prog. Chem. 2015, 27, 11-26.

Zhang, Y; Yu, J.; Wang, J.; Hanne, N. J.; Cui, Z.; Qian, C.; Wang, C.; Xin, H.; Cole, J. H.; Gallippi, C. M. Thrombin-Responsive Transcutaneous Patch for Auto-Anticoagulant Regulation. Adv. Mater. 2017, 29, 1604043.

We claim:

1. A particle consisting of i) an adipose tissue browning agent and/or fat modulating agent encapsulated in a pH-responsive matrix, ii) a pH altering agent, iii) a peroxide metabolizing enzyme, and iv) a surfactant.

2. The particle of claim 1, wherein the adipose tissue browning agent comprises rosiglitazone (Rosi), CL 316243, or combinations thereof.

3. The particle of claim 1, wherein the pH-altering agent comprises a glucose-responsive enzyme or glucose oxidase (GOx).

4. The particle of claim 1, wherein the peroxide-metabolizing enzyme comprises catalase (CAT).

5. The particle of claim 1, wherein the pH-responsive matrix comprises a polymer comprising dextran monomers.

6. The particle of claim 1, wherein the surfactant comprises alginate.

7. The particle of claim 6, wherein the alginate encapsulates a pH-responsive matrix.

8. A patch comprising the particle of claim 1.

9. A device for transport of a material across a biological barrier of a subject comprising:
   a plurality of microneedles each having a base end and a tip;
   a substrate to which the base ends of the microneedles are attached or integrated; and
   a plurality of particles comprising an adipose tissue browning agent and/or fat modulating agent.

10. The device of claim 9, wherein the plurality of particles are attached to the plurality of microneedles.

11. The device of claim 9, wherein the plurality of microneedles comprise a biocompatible polymer; and wherein the biocompatible polymer comprises methacrylated hyaluronic acid (m-HA).

12. The device of claim 11, wherein the biocompatible polymer is crosslinked.

13. A method of therapeutically treating obesity, diabetes, or a cancer in a subject or locally delivering an adipose tissue browning agent and/or fat modulating agent to a subject the method comprising:
   a) providing a device for transport of a material across a biological barrier of a subject comprising: a plurality of microneedles each having a base end and a tip; a substrate to which the base ends of the microneedles are attached or integrated; and a plurality of particles comprising an adipose tissue browning agent and/or fat modulating agent; and
   b) administering the device to a subject in need of treating a disease or in need of an adipose tissue browning agent and/or fat modulating agent.

14. The method of claim 13, wherein the plurality of particles further comprises a pH altering agent and a pH-responsive matrix; wherein the pH altering agent decreases the pH within the nanoparticles, and wherein the decrease in pH degrades the pH-responsive matrix and releases the adipose tissue browning agent and/or fat modulating agent.

15. The method of claim 13, wherein the administering step b) modulates expression of one or more brown adipocyte genes.

16. The method of claim 15, wherein the one or more brown adipocyte genes comprise Ucp1, Dio2, Elovl3, Cidea, Pgc-1α, Cox7a1, or Cox8b.

17. The method of claim 13, wherein the administering step b) increases expression of adiponectin.

18. The method of claim 13, wherein the administering step b) increases expression of PPARγ target aP2.

19. The method of claim 13, wherein the administering step b) decreases expression of one or more white adipocyte genes.

* * * * *